(12) United States Patent
Tahri et al.

(10) Patent No.: US 10,081,618 B2
(45) Date of Patent: Sep. 25, 2018

(54) QUINOXALINONES AND DIHYDROQUINOXALINONES AS RESPIRATORY SYNCYTIAL VIRUS ATIVIRAL AGENTS

(71) Applicant: Janssen Sciences Ireland UC, Little Island, County Cork (IE)

(72) Inventors: Abdellah Tahri, Anderlecht (BE); Tim Hugo Maria Jonckers, Heist-op-den-Berg (BE); Pierre Jean-Marie-Bernard Raboisson, Rosieres (BE); Samuël Dominique Demin, Antwerp (BE)

(73) Assignee: Janssen Sciences Ireland UC, Little Island, Co Cork (IE)

( * ) Notice: Subject to any disclaimer, the term of this patent is extended or adjusted under 35 U.S.C. 154(b) by 303 days.

(21) Appl. No.: 14/764,138

(22) PCT Filed: Jan. 27, 2014

(86) PCT No.: PCT/EP2014/051465
§ 371 (c)(1),
(2) Date: Jul. 28, 2015

(87) PCT Pub. No.: WO2014/114776
PCT Pub. Date: Jul. 31, 2014

(65) Prior Publication Data
US 2017/0260166 A1    Sep. 14, 2017

(30) Foreign Application Priority Data

Jan. 28, 2013 (EP) .................................. 13152915

(51) Int. Cl.
| | |
|---|---|
| *C07D 403/06* | (2006.01) |
| *C07D 403/14* | (2006.01) |
| *C07D 471/04* | (2006.01) |
| *C07D 401/14* | (2006.01) |
| *C07D 417/14* | (2006.01) |
| *C07D 519/00* | (2006.01) |

(52) U.S. Cl.
CPC ......... *C07D 403/06* (2013.01); *C07D 401/14* (2013.01); *C07D 403/14* (2013.01); *C07D 417/14* (2013.01); *C07D 471/04* (2013.01); *C07D 519/00* (2013.01)

(58) Field of Classification Search
CPC ..................................................... C07D 403/06
See application file for complete search history.

(56) References Cited

FOREIGN PATENT DOCUMENTS

| WO | 2002026228 A1 | 4/2002 |
|---|---|---|
| WO | 2002062290 A2 | 8/2002 |
| WO | WO 2003/053344 A2 | 7/2003 |
| WO | WO 2010/103306 A1 | 9/2010 |
| WO | 2012080446 A1 | 6/2012 |

OTHER PUBLICATIONS

Greene, et al., "Protection for the Hydroxyl Group Including 1,2- and 1,3-diols." Protective Groups in Organic Synthesis, 3rd edition, pp. 119-121 (1999). XP002670712.
Wang, et al., "Respiratory syncytial virus fusion inhibitors. Part 5 : Optimization of benzimidazole substitution patterns towards derivatives with improved activity", Bioorganic & Medicinal Chemistry Letters, vol. 17 (16): pp. 4592-4598 (Jul. 17, 2007).
Wyde, et al., "CL387626 exhibits marked and unusual antiviral activity against respiratory syncytial virus in tissue culture and in cotton rats", Antiviral Research, vol. 38: pp. 31-42 (1998).
Keith D. Combrink, et al., "Respiratory Syncytial Virus Fusion Inhibitors. Part 6: An Examination of the Effect of Structural Variation of the Benzimidazol-2-one Heterocycle Moiety" Bioorganic & Medicinal Chemistry Letters, 2007, pp. 4784-4790, vol. 17, No. 17.

*Primary Examiner* — Paul V Ward

(57) ABSTRACT

Quinoxalinones and dihydroquinoxalinones having inhibitory activity on RSV replication and having the formula I Formula I

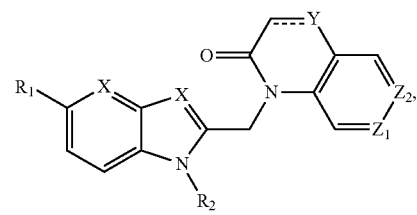

including addition salts, and stereochemically isomeric forms thereof; compositions containing these compounds as active ingredient and processes for preparing these compounds and compositions.

16 Claims, No Drawings

QUINOXALINONES AND DIHYDROQUINOXALINONES AS RESPIRATORY SYNCYTIAL VIRUS ATIVIRAL AGENTS

This application is a 35 U.S.C. § 371 nationalization of PCT application PCT/EP2014/051465 filed Jan. 27, 2014, which claims priority to European patent application EP 13152915.8 filed Jan. 28, 2013, both of which are incorporated herein by reference.

FIELD OF THE INVENTION

The invention concerns quinoxalinones and dihydroquinoxalinones having antiviral activity, in particular, having an inhibitory activity on the replication of the respiratory syncytial virus (RSV). The invention further concerns the preparation of these quinoxalinones and dihydroquinoxalinones, compositions comprising these compounds, and the compounds for use in the treatment of respiratory syncytial virus infection.

BACKGROUND

Human RSV or Respiratory Syncytial Virus is a large RNA virus, member of the family of Paramyxoviridae, subfamily pneumoviridae together with bovine RSV. Human RSV is responsible for a spectrum of respiratory tract diseases in people of all ages throughout the world. It is the major cause of lower respiratory tract illness during infancy and childhood. Over half of all infants encounter RSV in their first year of life, and almost all within their first two years. The infection in young children can cause lung damage that persists for years and may contribute to chronic lung disease in later life (chronic wheezing, asthma). Older children and adults often suffer from a (bad) common cold upon RSV infection. In old age, susceptibility again increases, and RSV has been implicated in a number of outbreaks of pneumonia in the aged resulting in significant mortality.

Infection with a virus from a given subgroup does not protect against a subsequent infection with an RSV isolate from the same subgroup in the following winter season. Re-infection with RSV is thus common, despite the existence of only two subtypes, A and B.

Today only three drugs have been approved for use against RSV infection. A first one is ribavirin, a nucleoside analogue, that provides an aerosol treatment for serious RSV infection in hospitalized children. The aerosol route of administration, the toxicity (risk of teratogenicity), the cost and the highly variable efficacy limit its use. The other two drugs, RespiGam® (RSV-IG) and Synagis® (palivizumab), polyclonal and monoclonal antibody immunostimulants, are intended to be used in a preventive way. Both are very expensive, and require parenteral administration.

Other attempts to develop a safe and effective RSV vaccine have all met with failure thus far. Inactivated vaccines failed to protect against disease, and in fact in some cases enhanced disease during subsequent infection. Life attenuated vaccines have been tried with limited success. Clearly there is a need for an efficacious non-toxic and easy to administer drug against RSV replication. It would be particularly preferred to provide drugs against RSV replication that could be administered perorally.

A reference related to benzimidazole antiviral agents is WO2012/080446. Herein compounds are presented to have anti-RSV activity. A reference on structure-activity relations, in respect of RSV inhibition, of 5-substituted benzimidazole compounds is X. A. Wang et al., Bioorganic and Medicinal Chemistry Letters 17 (2007) 4592-4598.

It is desired to provide new drugs that have antiviral activity. Particularly, it would be desired to provide new drugs that have RSV replication inhibitory activity. A further desire is to find compounds having oral antiviral activity.

SUMMARY OF THE INVENTION

In order to better address one or more of the foregoing desires, the invention, in one aspect, presents antiviral quinoxalinones and dihydroquinoxalinones compounds represented by formula I:

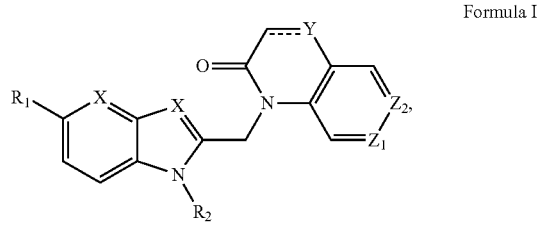

Formula I or a stereochemically isomeric or tautomeric form thereof wherein:
X independently is CH or N;
Y is N or N—$R_4$;
$Z_1$ is N or C—$R_6$;
$Z_2$ is N or C—$R_3$;
$R_1$ is selected from the group of H, halogen, $C_1$-$C_6$alkyl and $C_3$-$C_7$cycloalkyl;
$R_2$ is —$(CR_7R_8)_n$—$R_9$;
$R_3$ is selected from the group consisting of H, $C_1$-$C_6$alkyl, $C_3$-$C_7$cycloalkyl, $CF_3$ and halogen;
$R_4$ is selected from the group consisting of H, $C_1$-$C_6$alkyl and $C_3$-$C_7$cycloalkyl;
$R_6$ is selected from the group consisting of H, halogen, aryl and heteroaryl, wherein aryl or heteroaryl are optionally substituted with one or more $R_{10}$;
$R_7$ and $R_8$ are each independently chosen from H, $C_1$-$C_6$alkyl or $C_3$-$C_7$cycloalkyl;
$R_9$ is selected from the group consisting of H, halogen, $SO_2R_7$, $C_1$-$C_6$alkyl, $CONR_7R_8$, $COOR_7$, OH, CN, F, $CFH_2$, $CF_2H$ and $CF_3$;
$R_{10}$ is selected from the group consisting of H, OH, CN, halogen, $CFH_2$, $CF_2H$, $CF_3$, $CONR_7R_8$, $COOR_7$ and $C_1$-$C_6$ alkyl optionally substituted with one or more substituents selected from the group comprising $NR_7R_8$, $CF_3$, $CH_3$, $OCH_3$, $OCF_3$, morpholinyl or halogen;
or an addition salt or solvate thereof.

In a further aspect, the invention relates to a compound according to Formula I for use as a medicine.

In an additional aspect, the invention relates to a pharmaceutical composition comprising a pharmaceutically acceptable carrier, and as active ingredient a therapeutically effective amount of a compound according to Formula I.

In yet another aspect, the invention relates to a process for preparing a pharmaceutical composition according to the invention, said process comprising intimately mixing a pharmaceutically acceptable carrier with a therapeutically effective amount of a compound according to Formula I.

In a yet a further aspect, the invention relates to compounds of Formula I for use as a medicament for inhibiting RSV replication.

In another aspect, the invention relates to the foregoing compounds for use in the treatment of RSV infections in warm-blooded animals, preferably humans. In yet another aspect, the invention presents a method of treatment of viral RSV infections in a subject in need thereof, comprising administering to said subject an effective amount of a compound as defined above. In still another aspect, the invention resides in the use of a compound as defined above, for the manufacture of a medicament in the treatment of RSV infections.

In a further aspect, the invention relates to a pharmaceutical composition comprising a compound as defined above, and a pharmaceutically acceptable excipient.

In a still further aspect, the invention provides methods for preparing the compounds defined above.

DETAILED DESCRIPTION OF THE INVENTION

The molecules of formula I, in deviation from the prior art, have a quinoxalinone or dihydroquinoxalinone moiety. The invention, in a broad sense, is based on the judicious recognition that these compounds generally possess an interesting RSV inhibitory activity.

The present invention will further be described with respect to particular embodiments and with reference to certain examples but the invention is not limited thereto but only by the claims. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

As used herein $C_1$-$C_6$alkyl as a group or part of a group defines straight or branched chain saturated hydrocarbon radicals having from 1 to 6 carbon atoms such as methyl, ethyl, propyl, 1-methylethyl, butyl, pentyl, hexyl, 2-methylbutyl and the like.

$C_1$-$C_6$-alkoxy, as a group or part of a group defines an O—$C_1$-$C_6$alkyl radical, wherein $C_{1-6}$alkyl has, independently, the meaning given above.

$C_3$-$C_7$cycloalkyl is generic to cyclopropyl, cyclobutyl, cyclopentyl, cyclohexyl or cycloheptyl.

The term "aryl" means phenyl.

The term "heteroaryl" means a monocyclic- or polycyclic aromatic ring comprising carbon atoms, hydrogen atoms, and one or more heteroatoms, preferably, 1 to 3 heteroatoms, independently selected from nitrogen, oxygen, and sulfur. For the purposes of the invention, a heteroaryl group need only have some degree of aromatic character. Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3)- and (1,2,4)-triazolyl, pyrazinyl, pyrimidinyl, tetrazolyl, furyl, thienyl, isoxazolyl, thiazolyl, isoxazolyl, and oxazolyl. A heteroaryl group can be unsubstituted or substituted with one or two suitable substituents. Preferably, a heteroaryl group is a monocyclic ring, wherein the ring comprises 2 to 5 carbon atoms and 1 to 3 heteroatoms.

It should be noted that different isomers of the various heterocycles may exist within the definitions as used throughout the specification. For example, pyrrolyl may be 1H-pyrrolyl or 2H-pyrrolyl.

The term —$(CR_8R_9)_n$ used herein defines n repetitions of the $CR_8R_9$ subgroup, wherein each of these subgroups is independently defined. In particular, n is an integer 1 to 6.

The term halogen is generic to fluoro, chloro, bromo and iodo.

It should be noted that the radical positions on any molecular moiety used in the definitions may be anywhere on such moiety as long as it is chemically stable.

Radicals used in the definitions of the variables include all possible isomers unless otherwise indicated. For instance pentyl includes 1-pentyl, 2-pentyl and 3-pentyl.

When any variable occurs more than one time in any constituent, each definition is independent.

Whenever used hereinafter, the term "compounds of formula (I)", or "the present compounds" or similar term is meant to include the compounds of general formula (I), their prodrugs, N-oxides, addition salts, quaternary amines, metal complexes and stereochemically isomeric forms.

It will be appreciated that some of the compounds of formula (I) may contain one or more centers of chirality and exist as stereochemically isomeric forms.

The term "stereochemically isomeric forms" as used hereinbefore defines all the possible compounds made up of the same atoms bonded by the same sequence of bonds but having different three-dimensional structures which are not interchangeable, which the compounds of formula (I) may possess.

Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of the present invention both in pure form or in admixture with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i. e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric racemates of formula (I) can be obtained separately by conventional methods. Appropriate physical separation methods that may advantageously be employed are, for example, selective crystallization and chromatography, e.g. column chromatography.

For some of the compounds of formula (I), their prodrugs, N-oxides, salts, solvates, quaternary amines, or metal complexes and the intermediates used in the preparation thereof, the absolute stereochemical configuration was not experimentally determined.

A person skilled in the art is able to determine the absolute configuration of such compounds using art-known methods such as, for example, X-ray diffraction.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

For therapeutic use, salts of the compounds of formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove are meant to comprise the therapeutically active non-toxic acid and base addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butane-dioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salt as used hereinabove also comprises the solvates, which the compounds of formula (I) as well as the salts thereof, are able to form. Such solvates are for example hydrates, alcoholates and the like.

The term "quaternary amine" as used hereinbefore defines the quaternary ammonium salts which the compounds of formula (I) are able to form by reaction between a basic nitrogen of a compound of formula (I) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen.

Pharmaceutically acceptable counterions include chloro, bromo, iodo, trifluoroacetate and acetate. The counterion of choice can be introduced using ion exchange resins.

The N-oxide forms of the present compounds are meant to comprise the compounds of formula (I) wherein one or several nitrogen atoms are oxidized to the so-called N-oxide.

It will be appreciated that the compounds of formula (I) may have metal binding, chelating, complexating properties and therefore may exist as metal complexes or metal chelates. Such metalated derivatives of the compounds of formula (I) are intended to be included within the scope of the present invention.

Some of the compounds of formula (I) may also exist in their tautomeric form. Such forms although not explicitly indicated in the above formula are intended to be included within the scope of the present invention.

It will be appreciated that the compounds of the invention, with reference to the aforementioned left- and right-hand parts of formula I, present a wide variety of modification.

Without detracting from the overall scope of the invention, certain embodiments are discussed in more detail below.

The present invention relates to compounds satisfying formula I

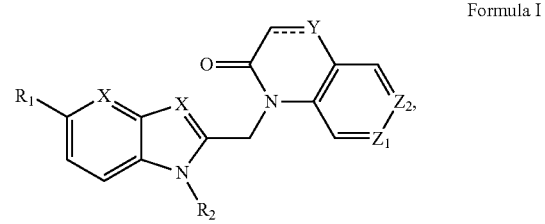

Formula I or a stereochemically isomeric or tautomeric form thereof wherein:

X independently is CH or N;
Y is N or N—$R_4$;
$Z_1$ is N or C—$R_6$;
$Z_2$ is N or C—$R_3$;
$R_1$ is selected from the group of H, halogen, $C_1$-$C_6$alkyl and $C_3$-$C_7$cycloalkyl;
$R_2$ is —$(CR_7R_8)_n$—$R_9$;
$R_3$ is selected from the group consisting of H, $C_1$-$C_6$alkyl, $C_3$-$C_7$cycloalkyl, $CF_3$ and halogen;
$R_4$ is selected from the group consisting of H, $C_1$-$C_6$alkyl and $C_3$-$C_7$cycloalkyl;
$R_6$ is selected from the group consisting of H, halogen, aryl and heteroaryl, wherein aryl or heteroaryl are optionally substituted with one or more $R_{10}$;
$R_7$ and $R_8$ are each independently chosen from H, $C_1$-$C_6$alkyl or $C_3$-$C_7$cycloalkyl;
$R_9$ is selected from the group consisting of H, halogen, $SO_2R_7$, $C_1$-$C_6$alkyl, $CONR_7R_8$, $COOR_7$, OH, CN, F, $CFH_2$, $CF_2H$ and $CF_3$;
$R_{10}$ is selected from the group consisting of H, OH, CN, halogen, $CFH_2$, $CF_2H$, $CF_3$, $CONR_7R_8$, $COOR_7$ and $C_1$-$C_6$ alkyl optionally substituted with one or more substituents selected from the group comprising $NR_7R_8$, $CF_3$, $CH_3$, $OCH_3$, $OCF_3$, morpholinyl or halogen;
or an addition salt or solvate thereof.

A preferred embodiment encompasses compounds of Formula I wherein $R_1$ is halogen.

One subgroup of compounds relates to compounds according to Formula I wherein $R_2$ is $C_1$-$C_6$alkyl, optionally substituted with one or more halogen or $SO_2R_7$.

Another subgroup of compounds relates to compounds according to Formula I wherein $R_2$ is —$(CR_7R_8)_n$—$R_9$ wherein $R_7$ and $R_8$ are each independently chosen from hydrogen, or $CH_3$, and n is an integer 3 or 4, and $R_9$ is halogen, $CF_3$ or $SO_2R_7$ wherein $R_7$ is $CH_3$.

Another subgroup of compounds according to the invention relates to compounds of Formula I wherein $R_6$ is selected from the group consisting of H, halogen and phenyl, pyridinyl, thiophenyl, pyrimidinyl, pyrazolyl, pyrrolyl, thiazolyl, each optionally substituted with one or more $R_{10}$.

Preferably, $R_{10}$ is selected from the group consisting of halogen and $C_1$-$C_3$ alkyl optionally substituted with one or more substituents selected from the group comprising $NR_7R_8$, $CF_3$, morpholinyl or halogen.

Even more preferably $R_6$ is selected from the group comprising phenyl, pyridinyl, thiophenyl, pyrimidinyl, pyrazolyl, pyrrolyl, thiazolyl, each optionally substituted with one halogen In yet another subgroup according to the invention, $R_2$ is $C_1$-$C_6$ alkyl optionally substituted with one or more F or $SO_2$-Me.

In an additional subgroup of compounds according to the invention, $R_3$ is hydrogen or halogen and $R_4$ is cyclopropyl or H.

In a preferred subgroup, one or more of the above indicated limitations are combined.

Preferred are compounds of Formula 1 wherein:
$R_1$ is halogen;
$R_2$ is $C_1$-$C_6$ alkyl, optionally substituted with one or more halogen or $SO_2R_7$;
$R_2$ is —$(CR_2R_8)_n$—$R_9$ wherein $R_7$ and $R_8$ are each independently chosen from hydrogen, or $CH_3$, and n is an integer 3 or 4, and $R_9$ is halogen, $CF_3$ or $SO_2R_7$ wherein $R_2$ is $CH_3$;
$R_2$ is —$(CR_7R_8)_n$—$R_9$ wherein $R_7$ and $R_8$ are hydrogen, n is an integer 4, and $R_9$ is fluoro or $CF_3$;
$R_2$ is —$(CR_7R_8)_n$—$R_9$ wherein $R_7$ and $R_8$ are hydrogen, n is an integer 4, and $R_9$ is $SO_2R_7$ wherein $R_2$ is $CH_3$;
$R_3$ is hydrogen or halogen, more preferably hydrogen or F;
$R_4$ is cyclopropyl or H;
$R_6$ is selected from the group consisting of H, halogen and phenyl, pyridinyl, thiophenyl, pyrimidinyl, pyrazolyl, pyrrolyl, thiazolyl, each optionally substituted with one or more $R_{10}$.

The present invention also relates to the following compounds formula I

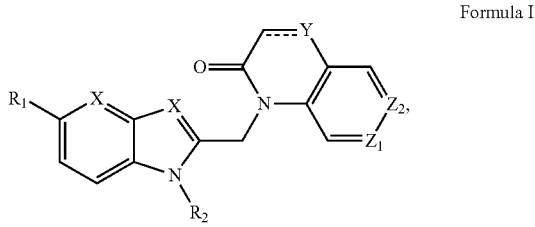

Formula I or a stereochemically isomeric or tautomeric form thereof wherein:

X independently is CH or N;
Y is N when ---- represents a double bond, or N—$R_4$ when ---- represent a single bond;
$Z_1$ is N or C—$R_6$;
$Z_2$ is N or C—$R_3$;
$R_1$ is halogen;
$R_2$ is —$(CR_7R_8)_n$—$R_9$ wherein n is an integer 3 or 4;
$R_3$ is selected from the group consisting of H and halogen;
$R_4$ is $C_3$-$C_7$cycloalkyl;
$R_6$ is selected from the group consisting of H, halogen, aryl and heteroaryl, wherein aryl or heteroaryl are optionally substituted with one or two substituents $R_{10}$;
$R_7$ and $R_8$ are each independently chosen from H, or $C_1$-$C_6$alkyl;
$R_9$ is selected from the group consisting of H, halogen, $SO_2R_7$, and $CF_3$;
$R_{10}$ is selected from the group consisting of H, $CF_3$, $COOR_7$ and $C_1$-$C_6$ alkyl optionally substituted with one substituent selected from the group comprising $NR_7R_8$ or morpholinyl;
aryl is phenyl;
heteroaryl is selected from pyridinyl, pyrimidinyl, thiophenyl, pyrrolyl, pyrazolyl, or thiazolyl;
or an addition salt or solvate thereof.

The compounds of formula I can be prepared by the methods described below, using synthetic methods known in the art of organic chemistry, or modifications and derivatisations that are familiar to those skilled in the art. The starting materials used herein are commercially available or may be prepared by routine methods known in the art such as those methods disclosed in standard reference books. Preferred methods include, but are not limited to, those described below.

During any of the following synthetic sequences it may be necessary and/or desirable to protect sensitive or reactive groups on any of the molecules concerned. This can be achieved by means of conventional protecting groups, such as those described in T. W. Greene and P. G. M. Wuts, Protective Groups in Organic Chemistry, John Wiley & Sons, 1999, which are hereby incorporated by reference.

Compounds of formula I, or their pharmaceutically acceptable salts, can be prepared according to the reaction schemes discussed herein below. Unless otherwise indicated, the substituents in the schemes are defined as above. Isolation and purification of the products is accomplished by standard procedures, which are known to a chemist of ordinary skill.

General Synthetic Schemes

The compounds of formula I may be prepared by the methods described below, using synthetic methods known in the art of organic chemistry, or modifications and derivatisations that are familiar to those skilled in the art. The starting materials used herein are commercially available or may be prepared by routine methods known in the art such as those methods disclosed in standard reference books. Preferred methods include, but are not limited to, those described below.

During any of the following synthetic sequences it may be necessary and/or desirable to protect sensitive or reactive groups on any of the molecules concerned. This can be achieved by means of conventional protecting groups, such as those described in T. W. Greene and P. G. M. Wuts, Protective Groups in Organic Chemistry, John Wiley & Sons, 1999, which are hereby incorporated by reference.

Compounds of formula I, or their pharmaceutically acceptable salts, can be prepared according to the reaction schemes discussed herein below. Unless otherwise indicated, the substituent in the schemes are defined as above.

Isolation and purification of the products is accomplished by standard procedures, which are known to a chemist of ordinary skill.

Scheme 1 illustrates a method for the preparation of compounds of formula I, where $R_1$ to $R_4$, X and Y are defined as above.

Referring to scheme 1, a compound of formula I can be synthesized by coupling 2-hydroxymethylene imidazopyridines II-a with quinoxalinones or dihydroquinoxalinones III in a known in the art method such as a Mitsunobu reaction which uses azadiisopropyldicarboxylate and triphenyl phosphine in a suitable solvent such as DMF or THF. Alternatively, compound of formula I may be prepared by displacement of Z, which is a halide, preferably chlorine II-b, or a sulfonate such as mesylate II-c in the presence of a base such as sodium hydride, potassium carbonate or cesium carbonate in a suitable solvent such as DMF or THF.

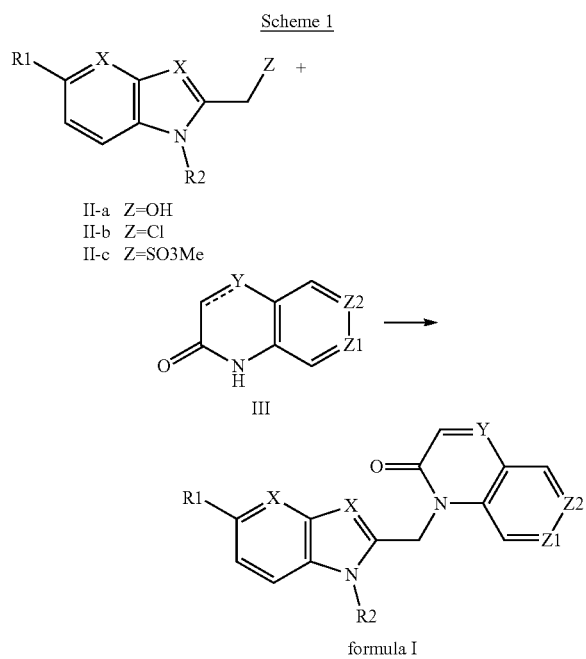

Preparation of Compound II-b and II-c

Treatment of the alcohol II-a with thionyl chloride provides 2-chloromethyl intermediates II-b. Alternatively, alcohol II-a may be transformed to the intermediate II-c by a reaction with methane sulfonyl chloride in the presence of an organic base such as triethyl amine or diisopropyl ethyl amine in a suitable solvent such as dichloromethane (scheme 2).

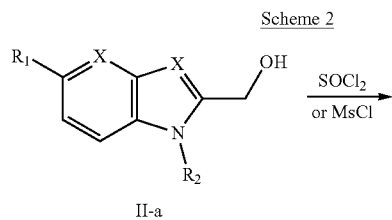

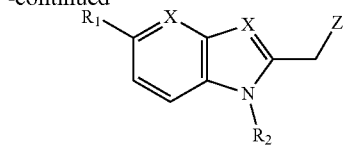

II-b  Z = Cl
II-c  Z = SO₃Me

Preparation of Compound II-a

Compounds of formula II-a are either commercially available or can be prepared, but not limited to, by general procedures illustrated by scheme 3, wherein $R_1$, $R_2$, X are defined as above. Referring to scheme 3 below, haloheteroaryls IV, where W is an halide preferably fluorine, can be treated with primary amines of formula V in the presence of a suitable base such as potassium carbonate and the like, in a suitable solvent such as ethanol or dichloromethane at a reaction temperature ranging from room temperature to 100° C. to give compounds of formula VI. Hydrogenation of the nitro group using well-precedented conditions such as Pd/C, or other catalyst, under hydrogen or Fe/EtOH/CaCl₂ can yield diamine of formula VII. Alternatively, the hydrogenation of the nitro group of compound VIII using well-precedented conditions such as Pd/C, or other catalyst, under hydrogen or Fe/EtOH/CaCl₂ yield diamine of formula IX which can be treated with the aldehydes of formula X in the presence of suitable reducing agents such as NaBH(OAc)₃, or Na(CN)BH₃ in solvents such as methylene chloride, DMF or THF, at about room temperature gives compounds of formula VII. The imidazol ring can be formed by treating diamines VII with glycolic acid or an ester like XIII under strong acidic conditions, such as aqueous hydrochloric acid, at elevated temperature such as reflux to yield the alcohols of formula II-a. Alternatively, diamines VII can be condensed with dialkoxyacetate of formula XII, in the presence of acetic acid, in a suitable solvent such as methanol gives the acetal II-e. The acetal of compounds II-e can be removed with acids such as hydrochloric acid to give the aldehydes of formula II-f. The resulting aldehydes of formula II-f can be reduced to alcohols using a suitable reducing agent such as NaBH₄ or LiAlH₄ in a suitable solvent such as ethanol or THF to yield the desired alcohols of formula II-a. In addition, diamines VII can be cyclize with dialkyl oxalate of formula XI in a suitable solvent such as ethanol at elevated temperature with or without microwave heating to produce imidazoles of formula II-d. Alternatively, compounds of formula II-d may be prepared in two steps synthesis starting from diamines VII. Firstly diamine VII may be reacted with an alkyl trihaloacetimidate, preferably methyl 2,2,2-trichloroacetimidate, in an acidic media, preferably acetic acid, at a temperature ranging between 25 and 50° C. to yield compounds of formula II-g. Secondly a reaction of compounds of formula II-g with metalcarbonate, preferably sodium carbonate in a suitable solvent such as methanol, leads to compounds of formula II-d. Compounds II-d can be subsequently reduced to the desired alcohols of formula II-a using a suitable reducing agent such as NaBH₄ or LiAlH₄ in a suitable solvent such as ethanol or THF.

Scheme 3

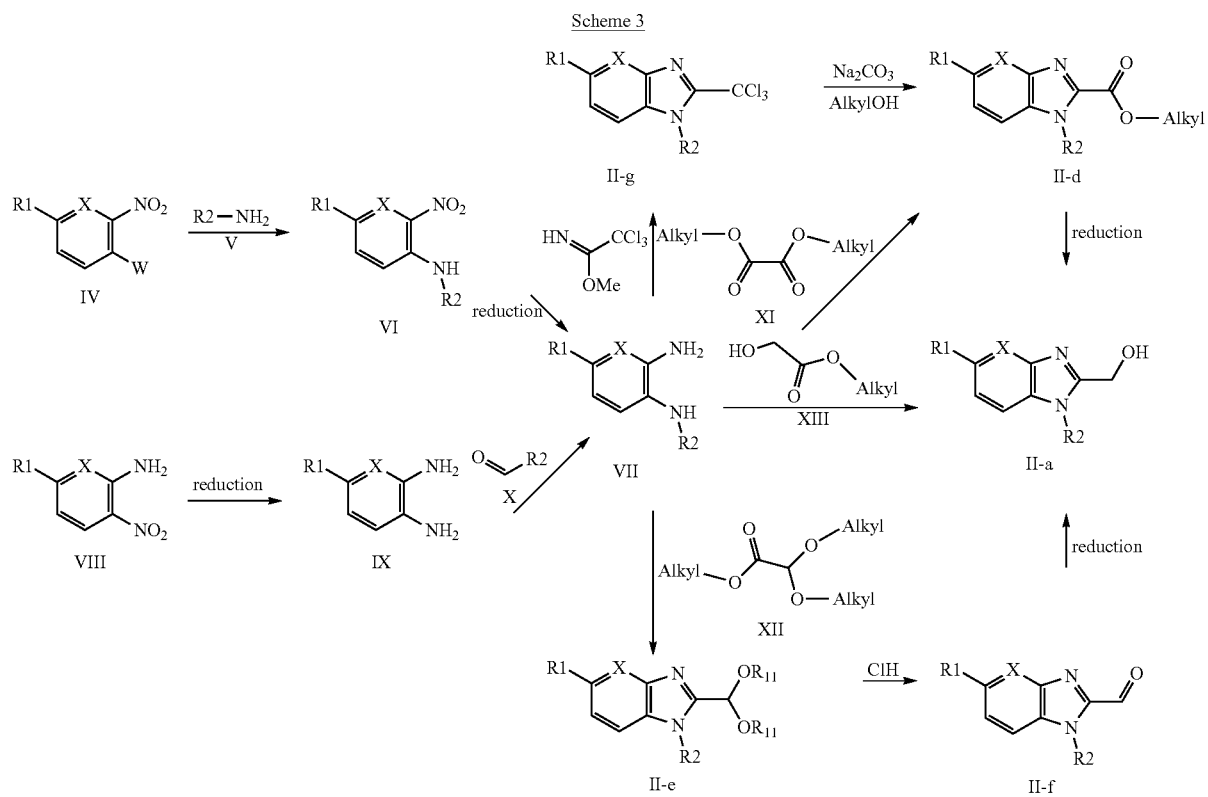

An alternative route for the preparation of compounds of type II-a is depicted in scheme 4. Diamine IX may be first coupled to an alkyl glycolic acid or an ester like XIII under strong acidic conditions, such as aqueous hydrochloric acid, at elevated temperature such as reflux to yield the alcohols of formula XIV. This alcohol may be protected by a PG, where PG is a protecting group such as, but not limiting to, a trityl which consequently results in compounds XV. A suitable solvent for this type of reactions can be, but not limiting to, dichloromethane. The treatment of compound XV with compound XVI, wherein the LG is a leaving group, such as halide, preferably bromine, or sulfonate, in the presence of a base such as sodium hydride, potassium carbonate or cesium carbonate in a suitable solvent such as DMF or THF, gives compound II-h. The removal of the PG in compound II-h may be done in the presence of an acid such as hydrochloric acid in the presence of a solvent, not limited to, such as dioxane to yield compound II-a.

Scheme 4

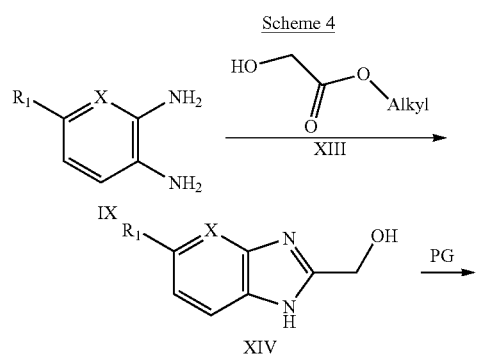

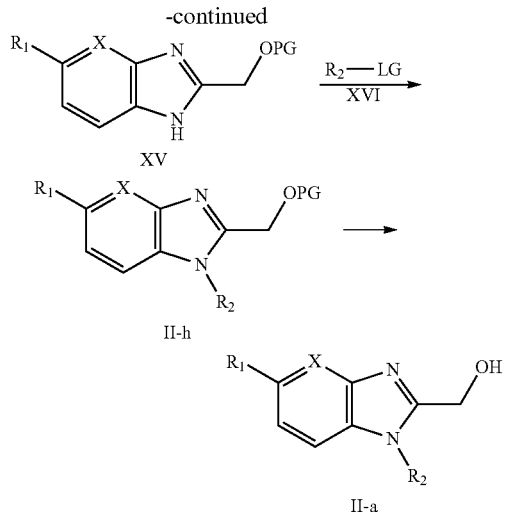

The Synthesis of quinoxalinones and pyridopyrazinones is shown in scheme 5. Compounds III can be synthesized using the procedure depicted in scheme 5. Commercially available nitroamino compounds of formula XXII can be reduced to the bis-amino compounds of formula XXIII in a catalytic way using hydrogen in the presence of a catalyst such as palladium or platinum, in a suitable solvent such as methanol, or in a stoichiometric way using iron in the presence of ammonium chloride or tin chloride in the presence of concentrated hydrochloric acid. The condensation of the resulting diamine compounds of formula XXIII with alkyl 2-oxoacetate compounds of formula XXIV, in a boiling solvent such as ethanol or isopropanol, gives the quinoxalinones and pyridopyrazinones compounds of formula III.

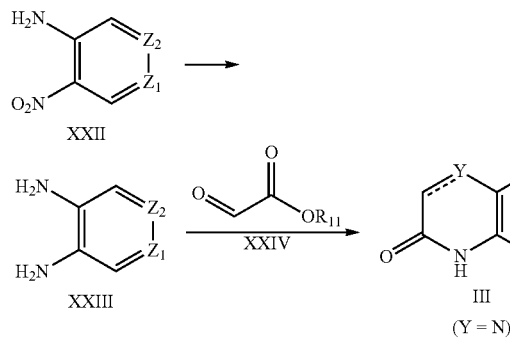

Scheme 5

The Synthesis of dihydropyridopyrazinones is shown in scheme 6. Displacement of W, which is a halide, preferably bromine or chlorine, of ester compounds of formula XVII with amine compounds of formula XVII, in a suitable solvent such as ethanol or butanol, gives compounds of formula XIX. The condensation of compounds of formula XIX with intermediate halonitro compounds of formula XX where X is a halide, preferably fluorine, or an alkoxy group, preferably methoxy, in a suitable solvent such as toluene, in the presence of an inorganic base such as cesium carbonate or potassium carbonate, gives compound XXI. Reduction of the nitro group can be done in a stoichiometric way using iron in the presence of ammonium chloride or tin chloride in the presence of concentrated hydrochloric acid to give the cyclised compounds of formula III.

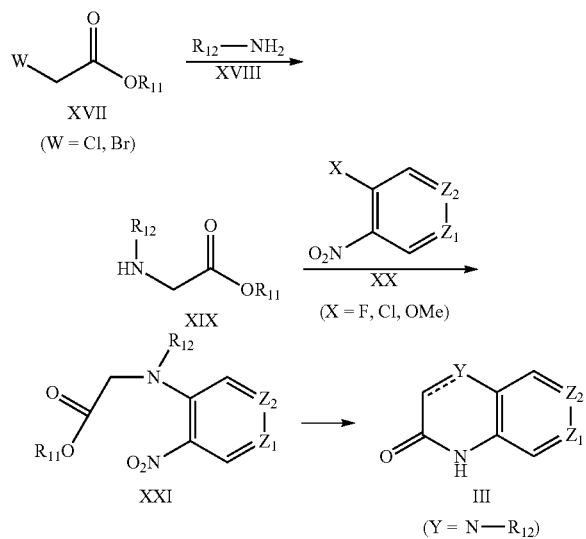

Scheme 6

Preparation of Compounds of Formula XXIV

Starting materials XXII used in this invention are commercially available, or can be synthesized, but not limited to, by methods known in the art such as Reissert synthesis or Fischer synthesis, reaction of such indoles with $R_2$-LG, where LG is a leaving group such as halide, preferably bromine, or sulfonate, in the presence of a base such as sodium hydride, potassium carbonate or cesium carbonate in a suitable solvent such as DMF or THF, gives compounds of formula XXIII (scheme 7). The conversion of the alkyl ester of compounds of formula XXIII to the alcohols of formula XXIV was carried out with metal hydride such as lithium aluminum hydride or sodium borohydride in a suitable solvent such as THF, methanol or ethanol.

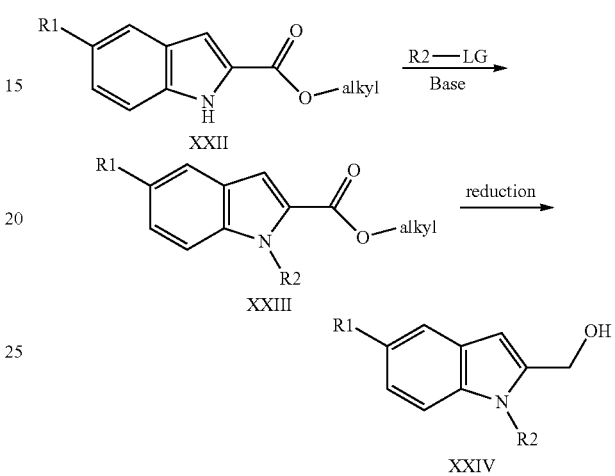

Scheme 7

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarbo-peroxoic acid, peroxoalkanoic acids, e.g. peroxoacetic acid, alkylhydroperoxides, e.g. t.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Pure stereochemically isomeric forms of the compounds of formula (I) may be obtained by the application of art-known procedures. Diastereomers may be separated by physical methods such as selective crystallization and chromatographic techniques, e.g., counter-current distribution, liquid chromatography and the like.

The compounds of formula (I) as prepared in the hereinabove described processes are generally racemic mixtures of enantiomers which can be separated from one another following art-known resolution procedures. The racemic compounds of formula (I) which are sufficiently basic or acidic may be converted into the corresponding diastereomeric salt forms by reaction with a suitable chiral acid, respectively chiral base. Said diastereomeric salt forms are subsequently separated, for example, by selective or fractional crystallization and the enantiomers are liberated therefrom by alkali or acid. An alternative manner of separating the enantiomeric forms of the compounds of formula (I)

involves liquid chromatography, in particular liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

In a further aspect, the present invention concerns a pharmaceutical composition comprising a therapeutically effective amount of a compound of formula (I) as specified herein, or a compound of any of the subgroups of compounds of formula (I) as specified herein, and a pharmaceutically acceptable carrier. A therapeutically effective amount in this context is an amount sufficient to prophylaxictically act against, to stabilize or to reduce viral infection, and in particular RSV viral infection, in infected subjects or subjects being at risk of being infected. In still a further aspect, this invention relates to a process of preparing a pharmaceutical composition as specified herein, which comprises intimately mixing a pharmaceutically acceptable carrier with a therapeutically effective amount of a compound of formula (I), as specified herein, or of a compound of any of the subgroups of compounds of formula (I) as specified herein.

Therefore, the compounds of the present invention or any embodiment thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form or metal complex, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

The compounds of the present invention may also be administered via oral inhalation or insufflation by means of methods and formulations employed in the art for administration via this way. Thus, in general the compounds of the present invention may be administered to the lungs in the form of a solution, a suspension or a dry powder, a solution being preferred. Any system developed for the delivery of solutions, suspensions or dry powders via oral inhalation or insufflation are suitable for the administration of the present compounds.

Thus, the present invention also provides a pharmaceutical composition adapted for administration by inhalation or insufflation through the mouth comprising a compound of formula (I) and a pharmaceutically acceptable carrier. Preferably, the compounds of the present invention are administered via inhalation of a solution in nebulized or aerosolized doses.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of formula (I) show antiviral properties. Viral infections treatable using the compounds and methods of the present invention include those infections brought on by ortho- and paramyxoviruses and in particular by human and bovine respiratory syncytial virus (RSV). A number of the compounds of this invention moreover are active against mutated strains of RSV. Additionally, many of the compounds of this invention show a favorable pharmacokinetic profile and have attractive properties in terms of bioavailability, including an acceptable half-life, AUC and peak values and lacking unfavourable phenomena such as insufficient quick onset and tissue retention.

The in vitro antiviral activity against RSV of the present compounds was tested in a test as described in the experimental part of the description, and may also be demonstrated in a virus yield reduction assay. The in vivo antiviral activity against RSV of the present compounds may be demonstrated in a test model using cotton rats as described in Wyde et al. (Antiviral Research (1998), 38, 31-42).

Due to their antiviral properties, particularly their anti-RSV properties, the compounds of formula (I) or any embodiment thereof, their prodrugs, N-oxides, addition salts, quaternary amines, metal complexes and stereochemically isomeric forms, are useful in the treatment of individuals experiencing a viral infection, particularly a RSV infection, and for the prophylaxis of these infections. In general, the compounds of the present invention may be useful in the treatment of warm-blooded animals infected with viruses, in particular the respiratory syncytial virus.

The compounds of the present invention or any embodiment thereof may therefore be used as medicines. Said use as a medicine or method of treatment comprises the systemic administration to viral infected subjects or to subjects susceptible to viral infections of an amount effective to combat the conditions associated with the viral infection, in particular the RSV infection.

The present invention also relates to the use of the present compounds or any embodiment thereof in the manufacture of a medicament for the treatment or the prevention of viral infections, particularly RSV infection.

The present invention furthermore relates to a method of treating a warm-blooded animal infected by a virus, or being at risk of infection by a virus, in particular by RSV, said method comprising the administration of an anti-virally effective amount of a compound of formula (I), as specified herein, or of a compound of any of the subgroups of compounds of formula (I), as specified herein.

In general it is contemplated that an antivirally effective daily amount would be from 0.01 mg/kg to 500 mg/kg body weight, more preferably from 0.1 mg/kg to 50 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines.

Also, the combination of another antiviral agent and a compound of formula (I) can be used as a medicine. Thus, the present invention also relates to a product containing (a) a compound of formula (I), and (b) another antiviral compound, as a combined preparation for simultaneous, separate or sequential use in antiviral treatment. The different drugs may be combined in a single preparation together with pharmaceutically acceptable carriers. For instance, the compounds of the present invention may be combined with interferon-beta or tumor necrosis factor-alpha in order to treat or prevent RSV infections.

The invention will hereinafter be illustrated with reference to the following, non-limiting examples.

Experimental Part

Synthesis of Intermediates

Synthesis of ethyl 1-cyclopropyl-1,2-dihydropyrido[4,3-b]pyrazin-3(4H)-one 4

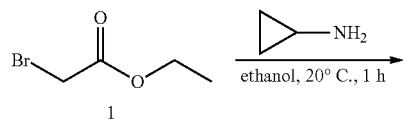

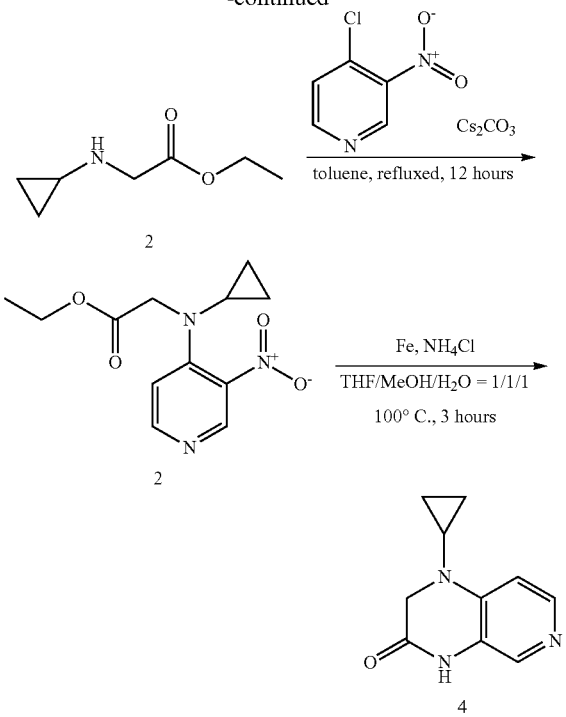

Step 1: Synthesis of ethyl 2-(cyclopropylamino) acetate 2

The commercially available cyclopropyl amine (348.6 g, 6736.5 mmol, 4.5 eq.) in ethanol (1500 ml) was stirred at 0° C. Ethylbromoacetate 1 (250 g, 1497 mmol, 1 eq.) was added dropwise. The mixture was allowed to warm to 20° C. and stirred for 1 hour. The solvent was removed under vacuum. The residue was dissolved in dichloromethane and washed with water. The organic layer was dried over $Na_2SO_4$ and concentrated under vacuum. 170 g of the title intermediate 2 was isolated (Yield: 79%).

Step 2: Synthesis of ethyl 2-(cyclopropyl(3-nitropyridin-4-yl)amino)acetate 3

The commercially available 4-chloro-3-nitropyridine (80 g, 504.6 mmol, 1 eq.), ethyl 2-(cyclopropylamino)acetate 2 (75.9 g, 529.8 mmol, 1.05 eq.) and Cesium carbonate (197.3 g, 605.5 mmol, 1.2 eq.) in toluene (800 ml) was refluxed for 12 hours. The mixture was filtered. The solvent was removed under vacuum. The residue was purified by column chromatography over silica gel (eluent: petroleum ether: ethyl acetate=1:1). 50 g of the title intermediate 3 was obtained. (Yield: 37.4%)

Step 3: Synthesis of ethyl 1-cyclopropyl-1,2-dihydropyrido[4,3-b]pyrazin-3(4H)-one 4

A mixture of intermediate 3 (50 g, 188.5 mmol, 1 eq.), iron (42.1 g, 754 mmol, 4 eq.) and ammonium chloride (40.3 g, 754 mmol, 4 eq.) in THF (500 ml), methanol (500 ml) and water (500 ml) was stirred at 100° C. for 3 hours. The mixture was filtrated. The organic solvent was removed under vacuum. The saturated aqueous $NaHCO_3$ was added until pH=9. The mixture was extracted with $CH_2Cl_2$ (2000 ml×5). The combined organic layer was washed with brine, dried over Na₂SO₄ and concentrated under vacuum. The residue was washed with t-butyl methyl ether and dried under vacuum. 25.5 g of the title intermediate 4 was obtained. (Yield: 71.5%)

Synthesis of 7-fluoroquinoxalin-2(1H)-one 6 and 6-fluoroquinoxalin-2(1H)-one 7

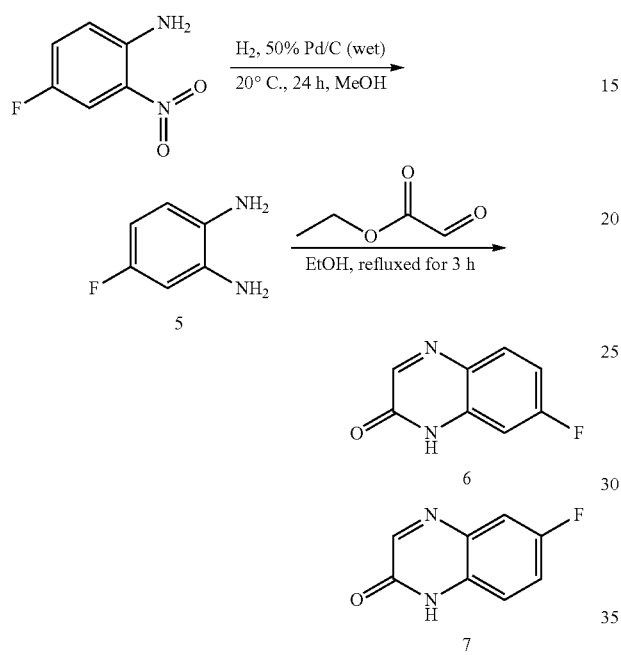

Step 1: Synthesis of 4-fluorobenzene-1,2-diamine 5

A solution of the commercially available 4-fluoro-2-nitro aniline (50 g, 320 mmol) in methanol (1000 ml) was hydrogenated with 50% Pd/C (10 g) as a catalyst at 20° C. (1 atm.) for 24 h. After uptake of H₂ (3 eq.), the catalyst was filtered off and the filtrate was evaporated. 49 g of the title intermediate 5 was obtained as black powder, (Yield purity 80%).

Step 2: Synthesis of 7-fluoroquinoxalin-2(1H)-one 6 and 6-fluoroquinoxalin-2(1H)-one 7

A solution of 4-fluorobenzene-1,2-diamine 5 (49 g, 320 mmol) in ethanol (500 ml) was stirred at 25° C. The mixture was cooled to 0° C. Ethyl 2-oxoacetate (24.48 g, 240 mmol) was added and stirred for 0.5 h at 0° C. The mixture was stirred and refluxed for 3 h at 120° C. The mixture was evaporated under vacuum. Dichloromethane (500 ml) was added and the mixture was stirred for 0.5 h at 25° C. The precipitate was filtered off. The solid was washed with tetrahydrofuran (300 ml×2) and washed with methanol (300 ml×2). The filtrate was evaporated to dryness under vacuum. The residue was washed with methyl t-butyl ether (100 ml). 5.8 g of a mixture (50/50) of intermediates 6 and 7 was obtained as brown powder (Yield 11.24%).

Synthesis of pyrido[3,4-b]pyrazin-3(4H)-one 9 and pyrido[4,3-b]pyrazin-2(1H)-one 10

Step 1: Synthesis of pyridine-3,4-diamine 8

The commercially available 3-nitropyridin-4-amine (50 g, 395 mmol) in the mixture of methanol (500 ml) and THF (500 ml) was hydrogenated with 10% Pd/C (5 g) as a catalyst at 10° C. (1 atm) for 24 h. After uptake of H₂ (3 eq), the catalyst was filtered off and the filtrate was evaporated. 38 g of the title intermediate 8 was obtained, (Yield 97%).

Step 2: Synthesis of pyrido[3,4-b]pyrazin-3 (4H)-one 9 and pyrido[4,3-b]pyrazin-2(1H)-one 10

The intermediate pyridine-3,4-diamine 8 (15 g, 137 mmol) was dissolved in ethanol (300 ml). ethyl 2-oxoacetate (30 g, 150 mmol) was added at 10° C. The mixture was stirred and refluxed for 3 h at 120° C. The reaction mixture was cooled to room temperature. The solid was washed with CH₃OH (2×100 ml) and evaporated under vacuum. 16 g of a mixture (50/50) of intermediates 9 and 10 was isolated (Yield 40%).

Synthesis of pyrazino[2,3-d]pyridazin-2(1H)-one 14

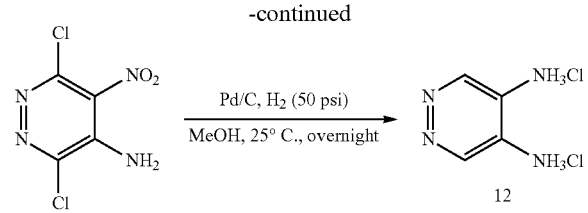

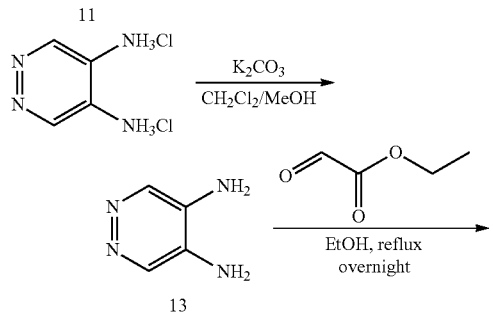

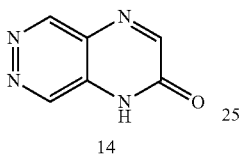

Step 1: Synthesis of 3,6-dichloro-5-nitropyridazin-4-amine 11

The commercially available 3,6-dichloropyridazine-4-amine (15 g, 92 mmol, 1 eq.) was added dropwise to the solution of fuming $HNO_3$ (12 ml, 290 mmol, 3.15 eq.) in conc. $H_2SO_4$ (60 ml) at 0° C. The mixture was stirred at 60° C. for 3 h. The reaction mixture was poured into crushed ice carefully, neutralized to pH=7 with aqueous NaOH solution. The solution was extracted with $CH_2Cl_2$, washed with brine, dried over $Na_2SO_4$. The solvent was removed under vacuum. The residue was washed with t-butyl methyl ether to give pure intermediate 11 (8.5 g, 45% yield).

Step 2: Synthesis of pyridazine-4,5-diaminium chloride 12

The Pd/C (5%, 5 g) was added to the mixture of intermediate 11 (17 g, 81.7 mmol, 1 eq.) in MeOH (1000 ml). The solution was stirred overnight at 25° C. under the atmosphere of $H_2$ (50 psi). The catalyst was filtered through a diatomite pad. The solvent was removed under vacuum. (15 g, crude yield 100%) of intermediate 12 was isolated.

Step 3: Synthesis of pyridazine-4,5-diamine 13

The potassium carbonate (22.6 g, 164 mmol, 2 eq.) was added to the mixture of intermediate 12 (15 g, 82 mmol, 1 eq.) in MeOH (150 ml) and $CH_2Cl_2$ (150 ml). The solution was stirred overnight at room temperature. The solution was filtered and the filtrate was concentrated under vacuum intermediate 13 was isolated (9 g, yield 95%).

Step 4: Synthesis of pyrazino[2,3-d]pyridazin-2(1H)-one 14

The mixture of intermediate 13 (4.6 g, 41.8 mmol, 1 eq.) and ethyl 2-oxoacetate (10.2 g, 50.1 mmol, 1.2 eq. 50% in toluene) in EtOH (240 ml) was stirred overnight at 80° C. The solvent was removed under vacuum. The residue was reflux for 3 h in $CH_3CN$, and then filtered to give pure intermediate 14 (3.07 g, yield 49.7%).

Synthesis of 2-(chloromethyl)-5-fluoro-1-(4-fluorobutyl)-1H-benzo[d]imidazole 16

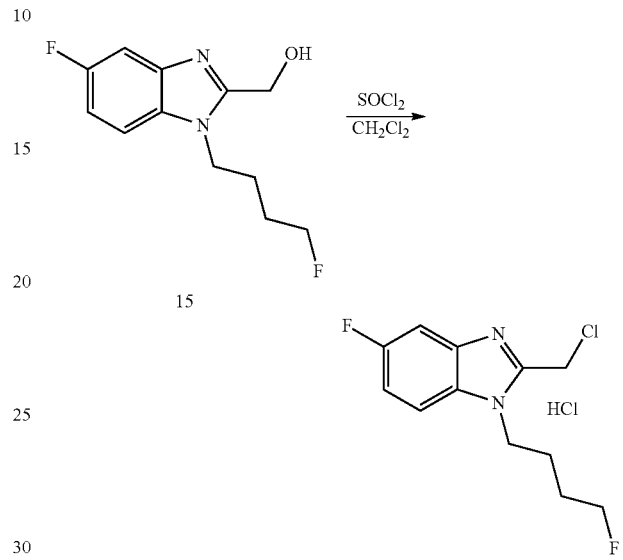

To a solution of alcohol 15 (prepared following the procedure described in WO2002/026228 A1) (363 mg, 1.414 mmole) in 30 mL of dichloromethane was added dropwise a solution of thionyl chloride (336 mg, 2 eq) in 10 mL of dichloromethane. The reaction mixture was stirred for one hour at 45° C. It was then concentrated under vacuum to give the desired intermediate 16 (440 mg, 99%) as an HCl salt, which was used as such in the next step.

EXAMPLES

Synthesis of 7-bromo-1-{[5-fluoro-1-(4-fluorobutyl)-1H-benzimidazol-2-yl]methyl}quinoxalin-2(1H)-one P1

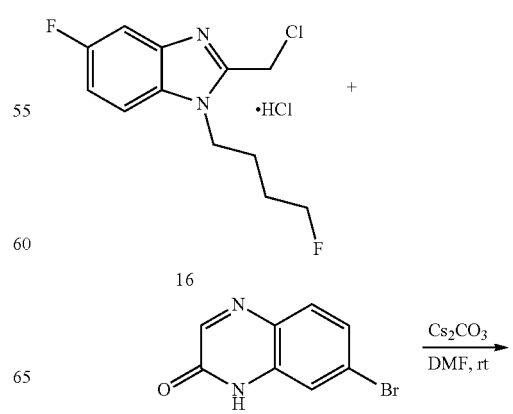

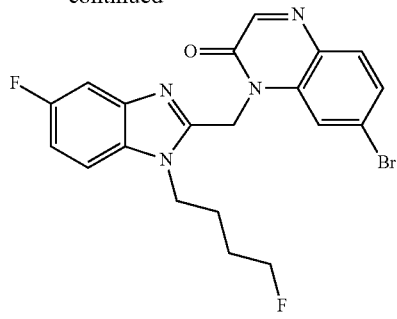

P1

2-(chloromethyl)-5-fluoro-1-(4-fluorobutyl)-1H-benzimidazole acid chloride salt 16 (4 g, 13.5 mmol) was dissolved in 100 ml DMF at room temperature. 7-bromoquinoxalin-2(1H)-one (CAS82031-32-1), (3.05 g, 13.5 mmol, 1 eq.) and $Cs_2CO_3$ (13 g, 40 mmol, 3 eq.) were added to the solution. The reaction mixture was stirred at room temperature for 16 hours. The reaction mixture was then diluted with water and extracted with dichloromethane. The combined organics were dried over $MgSO_4$ and evaporated. The residue was purified by Prep. HPLC on (RP Vydac Denali C18-10 μm, 200 g, 5 cm), using a 0.25% $NH_4HCO_3$ in water-$CH_3CN$ solution as eluent. After evaporation and drying in vacuo 3 g of product P1 (48%) was obtained.

LCMS m/z=447 (M+H)+

$^1$H NMR (400 MHz, CHLOROFORM-d) δ ppm 1.70-1.91 (m, 4H) 4.39 (t, J=7.65 Hz, 2H) 4.49 (dt, J=47.18, 5.27 Hz, 2H) 5.70 (s, 2H) 7.06 (td, J=9.10, 2.38 Hz, 1H) 7.24-7.30 (m, 1H) 7.43 (dd, J=9.29, 2.51 Hz, 1H) 7.48 (dd, J=8.53, 2.01 Hz, 1H) 7.73 (d, J=8.53 Hz, 1H) 8.35 (s, 1H) 8.38 (d, J=2.01 Hz, 1H)

General Procedure for the Synthesis of Compounds P2 to P8

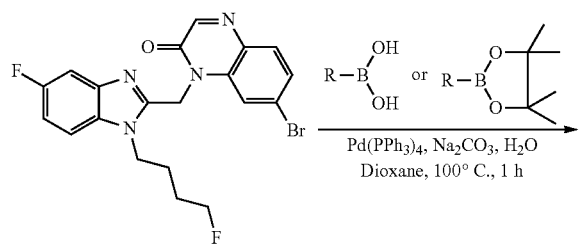

P1

To a solution of 7-bromo-1-{[5-fluoro-1-(4-fluorobutyl)-1H-benzimidazol-2-yl]-methyl} quinoxalin-2(1H)-one P1 (1 eq.) in water/dioxane (1/1) was added $Na_2CO_3$ (2.2 eq.), boronic acid or boronic ester (1.5 eq.) and Tetrakis(triphenylphosphine)-palladium (0.2 eq.) in a sealed microwave vial equipped by a magnetic stirrer. The reaction underwent microwave irradiation during 30 minutes at 100° C. The reaction mixture was diluted with water and extracted with dichloromethane. The combined extracts were dried over $MgSO_4$ and evaporated. The residue was purified by Prep. HPLC on (RP Vydac Denali C18-10 μm, 200 g, 5 cm) using a 0.25% $NH_4HCO_3$ in water-$CH_3CN$ solution as eluent, to give the end compounds (10 to 30% yield).

1-((5-fluoro-1-(4-fluorobutyl)-1H-benzo[d]imidazol-2-yl)methyl)-7-(4-(2-morpholinoethyl) phenyl)quinoxalin-2(1H)-one P2

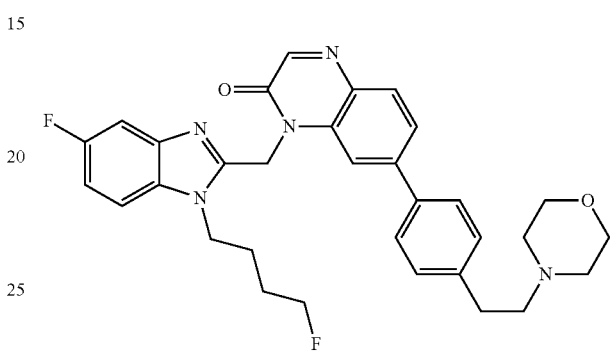

LCMS m/z=558 (M+H)+

$^1$H NMR (400 MHz, CHLOROFORM-d) δ ppm 1.71-1.84 (m, 4H) 2.51-2.60 (m, 4H) 2.63-2.70 (m, 2H) 2.84-2.93 (m, 2H) 3.72-3.82 (m, 4H) 4.32-4.42 (m, 3H) 4.51 (t, J=5.40 Hz, 1H) 5.85 (s, 2H) 7.06 (td, J=9.10, 2.38 Hz, 1H) 7.24-7.29 (m, 1H) 7.35 (d, J=8.28 Hz, 2H) 7.45 (dd, J=9.16, 2.38 Hz, 1H) 7.59 (dd, J=8.41, 1.63 Hz, 1H) 7.66 (d, J=8.03 Hz, 2H) 7.90 (d, J=8.28 Hz, 1H) 8.34 (s, 1H) 8.57 (d, J=1.76 Hz, 1H)

1-((5-fluoro-1-(4-fluorobutyl)-1H-benzo[d]imidazol-2-yl)methyl)-7-(4-(trifluoromethyl)phenyl)quinoxalin-2(1H)-one P3

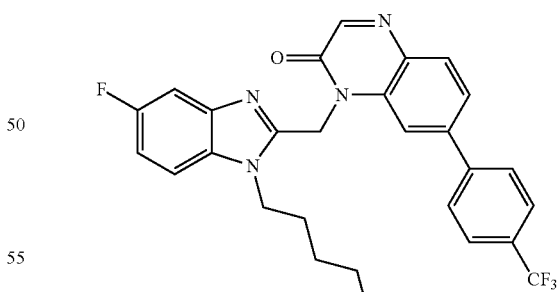

LCMS m/z=513 (M+H)+

$^1$H NMR (400 MHz, CHLOROFORM-d) δ ppm 1.69-1.91 (m, 4H) 4.34-4.44 (m, 3H) 4.52 (t, J=5.30 Hz, 1H) 4.55-4.55 (m, 0H) 5.85 (s, 2H) 7.06 (td, J=9.00, 2.26 Hz, 1H) 7.27-7.31 (m, 1H) 7.45 (dd, J=9.03, 2.26 Hz, 1H) 7.61 (dd, J=8.28, 1.76 Hz, 1H) 7.77 (br. d, J=8.30 Hz, 2H) 7.85 (br. d, J=8.30 Hz, 2H) 7.95 (d, J=8.28 Hz, 1H) 8.38 (s, 1H) 8.67 (d, J=1.76 Hz, 1H)

25

7-(2,4-dimethylthiazol-5-yl)-1-((5-fluoro-1-(4-fluorobutyl)-1H-benzo[d]imidazol-2-yl)methyl)quinoxalin-2(1H)-one P4

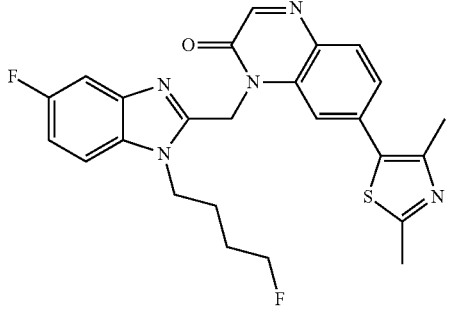 [SMILES: Cc1nc(C)c(-c2ccc3ncc(=O)n(Cc4nc5cc(F)ccc5n4CCCCF)c3c2)s1]

LCMS m/z=480 (M+H)+

$^1$H NMR (400 MHz, CHLOROFORM-d) δ ppm 1.71-1.84 (m, 4H) 2.49 (s, 3H) 2.72 (s, 3H) 4.35-4.44 (m, 3H) 4.52 (t, J=5.27 Hz, 1H) 5.78 (s, 2H) 7.05 (td, J=9.03, 2.51 Hz, 1H) 7.24-7.28 (m, 1H) 7.37-7.42 (m, 2H) 7.88 (d, J=8.28 Hz, 1H) 8.29 (d, J=1.76 Hz, 1H) 8.35 (s, 1H)

1-((5-fluoro-1-(4-fluorobutyl)-1H-benzo[d]imidazol-2-yl)methyl)-7-(1-methyl-3-(trifluoromethyl)-1H-pyrazol-5-yl)quinoxalin-2(1H)-one P5

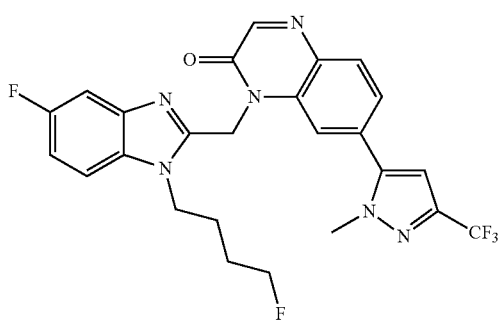 [SMILES: Cn1nc(C(F)(F)F)cc1-c1ccc2ncc(=O)n(Cc3nc4cc(F)ccc4n3CCCCF)c2c1]

LCMS m/z=517 (M+H)+

$^1$H NMR (400 MHz, CHLOROFORM-d) δ ppm 1.72-1.89 (m, 4H) 4.02 (s, 3H) 4.36-4.49 (m, 3H) 4.51-4.59 (m, 1H) 5.77 (s, 2H) 6.69 (s, 1H) 7.07 (td, J=9.00, 2.51 Hz, 1H) 7.26-7.31 (m, 1H) 7.32 (dd, J=9.03, 2.51 Hz, 1H) 7.43 (dd, J=8.16, 1.63 Hz, 1H) 7.98 (d, J=8.28 Hz, 1H) 8.41 (s, 1H) 8.43 (d, J=1.51 Hz, 1H).

26

1-((5-fluoro-1-(4-fluorobutyl)-1H-benzo[d]imidazol-2-yl)methyl)-7-phenylquinoxalin-2(1H)-one P6

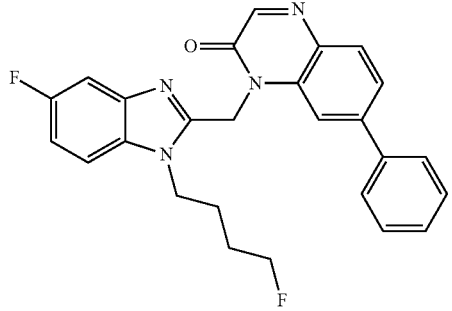

LCMS m/z=445 (M+H)+

$^1$H NMR (400 MHz, CHLOROFORM-d) δ ppm 1.67-1.84 (m, 4H) 4.28-4.43 (m, 3H) 4.45-4.55 (m, 1H) 5.85 (s, 2H) 7.05 (td, J=9.30, 2.51 Hz, 1H) 7.25-7.28 (m, 1H) 7.41-7.47 (m, 2H) 7.48-7.54 (m, 2H) 7.61 (dd, J=8.53, 2.01 Hz, 1H) 7.69-7.76 (m, 2H) 7.90 (d, J=8.53 Hz, 1H) 8.36 (s, 1H) 8.58 (d, J=1.76 Hz, 1H)

7-(3-((dimethylamino)methyl)phenyl)-1-((5-fluoro-1-(4-fluorobutyl)-1H-benzo[d]imidazol-2-yl)methyl)quinoxalin-2(1H)-one P7

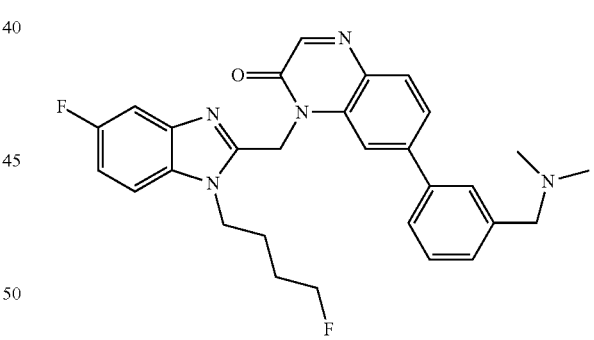

LCMS m/z=502 (M+H)+

$^1$H NMR (400 MHz, CHLOROFORM-d) δ ppm 1.69-1.84 (m, 4H) 2.31 (s, 6H) 3.55 (s, 2H) 4.29-4.43 (m, 3H) 4.51 (t, J=5.52 Hz, 1H) 5.87 (s, 2H) 7.07 (td, J=9.00, 2.76 Hz, 1H) 7.24-7.29 (m, 1H) 7.32-7.39 (m, 1H) 7.45 (t, J=7.65 Hz, 1H) 7.49 (dd, J=9.29, 2.26 Hz, 1H) 7.57-7.65 (m, 2H) 7.71 (br. s, 1H) 7.90 (d, J=8.28 Hz, 1H) 8.35 (s, 1H) 8.60 (d, J=1.76 Hz, 1H)

1-((5-fluoro-1-(4-fluorobutyl)-1H-benzo[d]imidazol-2-yl)methyl)-7-(pyridin-4-yl)quinoxalin-2(1H)-one P8

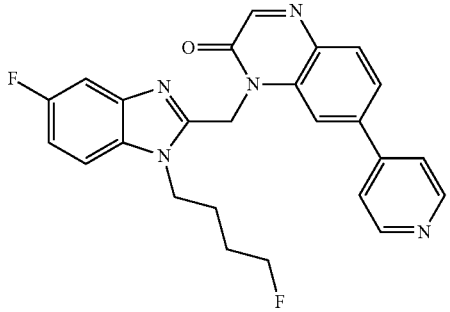

LCMS m/z=446 (M+H)+
$^1$H NMR (400 MHz, CHLOROFORM-d) δ ppm 1.72-1.85 (m, 4H) 4.34-4.44 (m, 3H) 4.50-4.55 (m, 1H) 5.86 (s, 2H) 7.07 (td, J=9.30, 2.26 Hz, 1H) 7.27-7.30 (m, 1H) 7.45 (dd, J=9.16, 2.38 Hz, 1H) 7.62-7.68 (m, 3H) 7.97 (d, J=8.28 Hz, 1H) 8.40 (s, 1H) 8.71-8.79 (m, 3H)

Synthesis of 7-fluoro-1-((5-fluoro-1-(4-fluorobutyl)-1H-benzo[d]imidazol-2-yl)methyl)quinoxalin-2(1H)-one P9 and 6-fluoro-1-((5-fluoro-1-(4-fluorobutyl)-1H-benzo[d]imidazol-2-yl) methyl)quinoxalin-2 (1H)-one P10

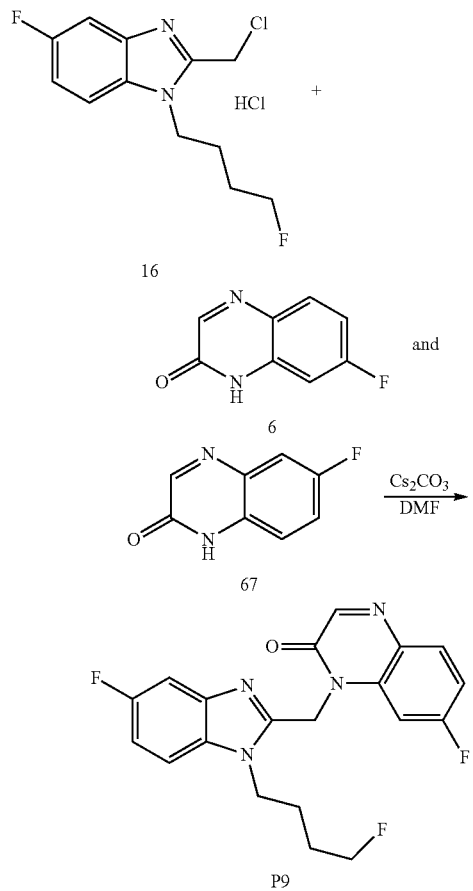

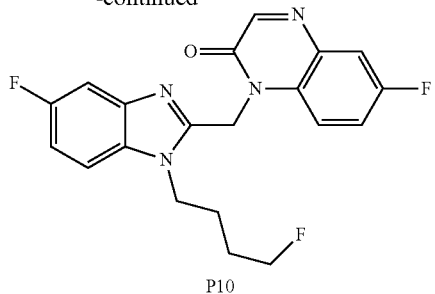

2-(chloromethyl)-5-fluoro-1-(4-fluorobutyl)-1H-benzimidazole acid chloride salt 16 (1 g, 3.38 mmol) was dissolved in 100 ml DMF at room temperature. The mixture of 7-fluoroquinoxalin-2(1H)-one 6 and 6-fluoroquinoxalin-2(1H)-one 7 (666 mg, 4 mmol, 1.2 eq.) and Cs$_2$CO$_3$ (3.3 g, 10 mmol, 3 eq.) were added to the solution. The reaction mixture was stirred at room temperature for 16 hours. The reaction mixture was then diluted with water and extracted with dichloromethane. The combined organics were dried over MgSO$_4$. The solvent was removed and the residue was purified by Prep.

HPLC on (RP Vydac Denali C18-10 μm, 200 g, 5 cm), using a 0.25% NH$_4$HCO$_3$ in water-CH$_3$CN solution as eluent and by SFC to yield the end products P9 (350 mg, 26%) and P10 (420 mg, 30%).

7-fluoro-1-((5-fluoro-1-(4-fluorobutyl)-1H-benzo[d]imidazol-2-yl)methyl)quinoxalin-2(1H)-one P9

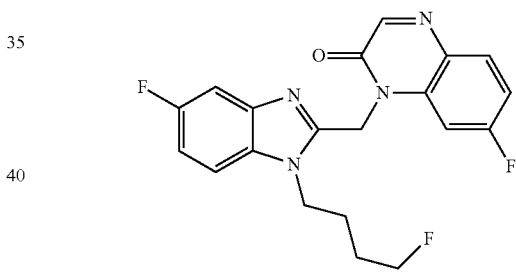

LCMS m/z=387 (M+H)+
$^1$H NMR (400 MHz, DMSO-d$_6$) δ ppm 1.69-1.85 (m, 2H), 1.86-1.97 (m, 2H), 4.38-4.49 (m, 3H), 4.57 (t, J=5.8 Hz, 1H), 5.72 (s, 2H), 7.06-7.15 (m, 1H), 7.23-7.36 (m, 2H), 7.59-7.70 (m, 2H), 7.95 (dd, J=8.9, 6.1 Hz, 1H), 8.30 (s, 1H)

6-fluoro-1-((5-fluoro-1-(4-fluorobutyl)-1H-benzo[d]imidazol-2-yl)methyl)quinoxalin-2(1H)-one P10

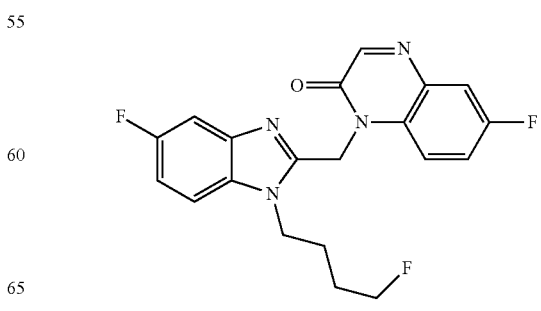

LCMS m/z=387 (M+H)+

¹H NMR (400 MHz, DMSO-d₆) δ ppm 1.67-1.84 (m, 2H), 1.85-1.95 (m, 2H), 4.39-4.49 (m, 3H), 4.57 (t, J=5.8 Hz, 1H), 5.73-5.82 (m, 2H), 7.11 (td, J=9.3, 2.5 Hz, 1H), 7.31 (dd, J=9.8, 2.3 Hz, 1H), 7.55 (td, J=8.8, 3.0 Hz, 1H), 7.64 (dd, J=8.9, 4.6 Hz, 1H), 7.70-7.80 (m, 2H), 8.41 (s, 1H)

1-((5-fluoro-1-(4-fluorobutyl)-1H-benzo[d]imidazol-2-yl)methyl)pyrido[3,4-b]pyrazin-2(1H)-one P11

Compound P11 was prepared by an analogous reaction protocol as compound P9 using intermediate 16 and pyrido[4,3-b]pyrazin-2(1H)-one 10 as starting material.

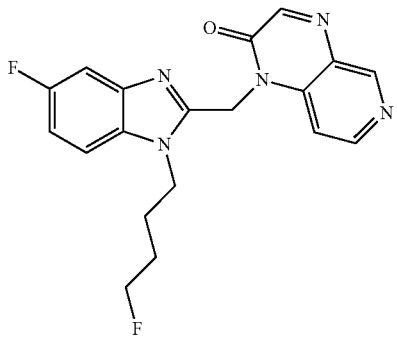 [SMILES: O=c1cnc2cnccc2n1Cc1nc2cc(F)ccc2n1CCCCF]

LCMS m/z=370 (M+H)+

¹H NMR (400 MHz, DMSO-d₆) δ ppm 1.70-1.87 (m, 2H), 1.87-1.99 (m, 2H), 4.37-4.51 (m, 3H), 4.58 (t, J=5.9 Hz, 1H), 5.73 (s, 2H), 7.12 (td, J=9.3, 2.5 Hz, 1H), 7.31 (dd, J=9.8, 2.3 Hz, 1H), 7.60-7.70 (m, 2H), 8.42 (s, 1H), 8.61 (d, J=5.8 Hz, 1H), 9.05 (s, 1H)

1-cyclopropyl-4-((5-fluoro-1-(4-fluorobutyl)-1H-benzo[d]imidazol-2-yl)methyl)-1,2-dihydropyrido[3,4-b]pyrazin-3(4H)-one P12

Compound P12 was prepared by an analogous reaction protocol as compound P9 using intermediate 16 and ethyl 1-cyclopropyl-1,2-dihydropyrido[4,3-b]pyrazin-3(4H)-one 4 as starting material.

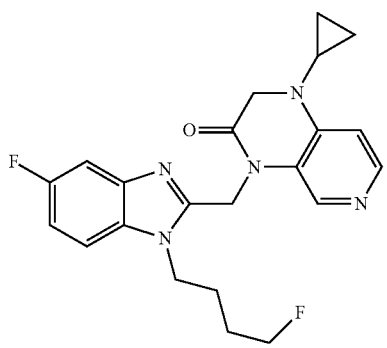 [SMILES: O=C1CN(C2CC2)c2ccncc2N1Cc1nc2cc(F)ccc2n1CCCCF]

LCMS m/z=412 (M+H)+

¹H NMR (400 MHz, CHLOROFORM-d) δ ppm 0.66 (m, J=3.6, 1.6 Hz, 2H), 0.94 (m, J=6.5, 1.8 Hz, 2H), 1.67-1.84 (m, 2H), 1.87 (m, J=7.3 Hz, 2H), 2.34-2.42 (m, 1H), 4.04 (s, 2H), 4.24-4.33 (m, 2H), 4.42 (t, J=5.6 Hz, 1H), 4.53 (t, J=5.5 Hz, 1H), 5.42 (s, 2H), 6.98-7.05 (m, 2H), 7.22 (dd, J=8.9, 4.4 Hz, 1H), 7.38 (dd, J=9.4, 2.4 Hz, 1H), 8.16 (d, J=5.3 Hz, 1H), 8.62 (s, 1H)

Synthesis of 7-bromo-1-((5-chloro-1-isopentyl-1H-imidazo[4,5-b]pyridin-2-yl)methyl)quinoxalin-2(1H)-one P13

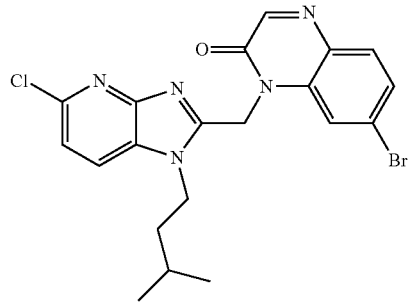 [SMILES: CC(C)CCn1c(Cn2c(=O)cnc3ccc(Br)cc32)nc2nc(Cl)ccc21]

Step 1: Synthesis of 6-chloropyridine-2,3-diamine 17

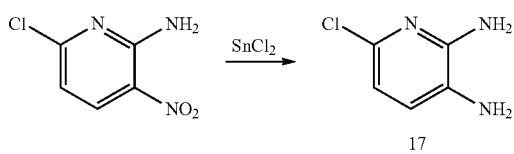

To a mixture of ethyl acetate (450 mL) and tert-butanol (50 mL), 6-chloro-3-nitropyridin-2-amine (CAS 27048-04-0) (15 g, 86.42 mmol), stannous chloride dehydrate (CAS 10025-69-1) (97.5 g, 432.1 mmol) were added. The resulting mixture was stirred at 60° C. for 1 hour. Sodiumborohydride (1.63 g, 43.21 mmol) was added and the mixture was stirred further at 60° C. for another 3 h. The mixture was cooled and stripped from the EtOAc on the rotavapor. The resulting residue was diluted with water (350 mL) and neutralized to pH=9-10 by addition of an aqueous solution of potassium carbonate. The resulting mixture was extracted with EtOAc (3×250 mL), dried over Na₂SO₄ and evaporated. The residue was stirred for 72 hours in a mixture of EtOAc/heptane 1/1. The precipitate was filtered and dried in vacuum for 2 hours. The intermediate 17 was collected as a greenish powder (9.32 g, 75%). m/z=144 (M+H)+.

Step 2: Synthesis of 6-chloro-N³-isopentylpyridine-2,3-diamine 18

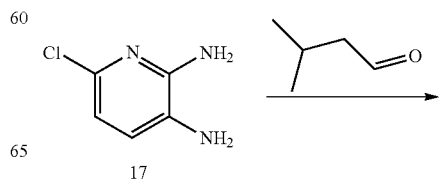

-continued

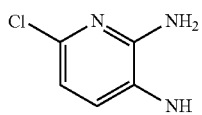

18

The intermediate 17 (5 g, 34.82 mmol) was dissolved in dichloromethane (200 mL), acetic acid (20 drops) and 4-methylpentanal (3 g, 34.8 mmol, CAS 1119-16-0) were added. The resulting mixture was stirred for 30 minutes and then sodium triacetoxy-hydroborate (22.14 g, 104.5 mmol) was added. The reaction mixture was stirred at room temperature overnight and a solution of 50% $Na_2CO_3$ was added dropwise until gas evolution stopped. The organic layer was separated, dried on $MgSO_4$, filtrated and evaporated to dryness. The residue was purified by column chromatography using heptane/EtOAc 7/3 to pure EtOAc. Compound 18 was recovered as a white solid and dried in vacuo overnight (4.8 g, 65%).

m/z=214 $(M+H)^+$.

Step 3: Synthesis of (5-chloro-1-isopentyl-1H-imidazo[4,5-b]pyridin-2-yl)methanol 19

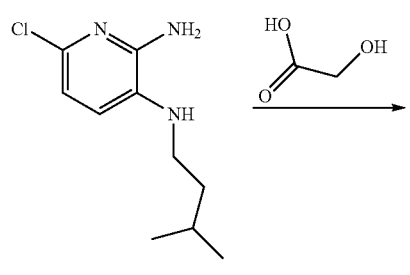

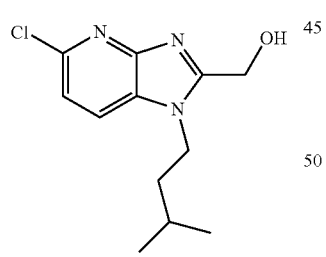

19

A mixture of intermediate 18 (4.8 g, 22.46 mmol) and 2-hydroxyacetic acid (4.27 g, 56.2 mmol) was stirred at 150° C. for 4 hours. The mixture was allowed to cool down to room temperature and treated carefully with 3N hydrochloric acid. The resulting mixture was made basic with aqueous ammonia and extracted with $CH_2Cl_2$ (300 mL). The organic layer was dried over $MgSO_4$ and evaporated to dryness. The residue was purified by column chromatography on silica using $CH_2Cl_2$ to EtOAc. The product 19 was isolated as brown solid (3.5 g, 61%).

m/z=255 $(M+H)^+$.

Step 4: Synthesis of 5-chloro-2-(chloromethyl)-1-isopentyl-1H-imidazo[4,5-b]pyridine hydrochloric acid 20

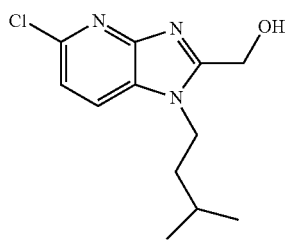 

19

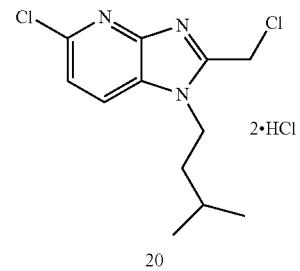

20

Intermediate 20 was prepared by an analogous reaction protocol as intermediate 16 using intermediate 19 as starting material.

Step 5: Synthesis of 7-bromo-1-((5-chloro-1-isopentyl-1H-imidazo[4,5-b]pyridin-2-yl)methyl) quinoxalin-2(1H)-one P13

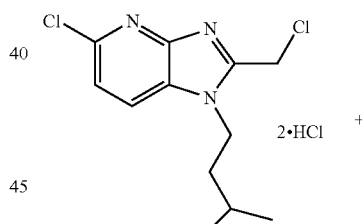

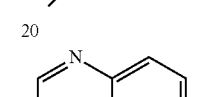

P13

Compound P13 was prepared by an analogous reaction protocol as compound P1 using intermediate 20 and 7-bromoquinoxalin-2(1H)-one (CAS82031-32-1) as starting material.

LCMS m/z=460 (M+H)$^+$ $^1$H NMR (400 MHz, CHLOROFORM-d) δ ppm 0.92-1.15 (m, 6H), 1.60 (br. s., 2H), 1.70-1.89 (m, 1H), 4.40 (br. s., 2H), 5.68 (br. s., 2H), 7.16-7.35 (m, 1H), 7.48 (d, J=7.8 Hz, 1H), 7.62 (d, J=8.0 Hz, 1H), 7.72 (d, J=7.8 Hz, 1H), 8.18 (br. s., 1H), 8.31 (br. s., 1H).

Compounds P14 to P18 were prepared by an analogous reaction protocol as compound P2 using Compound P13 and different boronic acids as starting material.

1-((5-chloro-1-isopentyl-1H-imidazo[4,5-b]pyridin-2-yl)methyl)-7-(pyridin-4-yl)quinoxalin-2(1H)-one P14

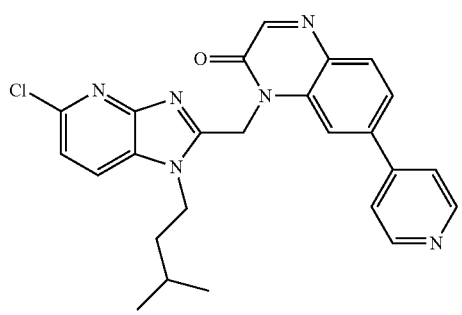 [SMILES: CC(C)CCn1c(Cn2c(=O)cnc3ccc(-c4ccncc4)cc32)nc2nc(Cl)ccc21]

LCMS m/z=459 (M+H)$^+$ $^1$H NMR (400 MHz, CHLOROFORM-d) δ ppm 1.01 (d, J=6.53 Hz, 6H) 1.47-1.58 (m, 2H) 1.68-1.79 (m, 1H) 4.30-4.53 (m, 2H) 5.84 (s, 2H) 7.16-7.31 (m, 2H) 7.59-7.68 (m, 3H) 7.97 (d, J=8.28 Hz, 1H) 8.37 (s, 1H) 8.54 (d, J=1.76 Hz, 1H) 8.74-8.78 (m, 2H).

1-((5-chloro-1-isopentyl-1H-imidazo[4,5-b]pyridin-2-yl)methyl)-7-(thiophen-3-yl)-quinoxalin-2(1H)-one P15

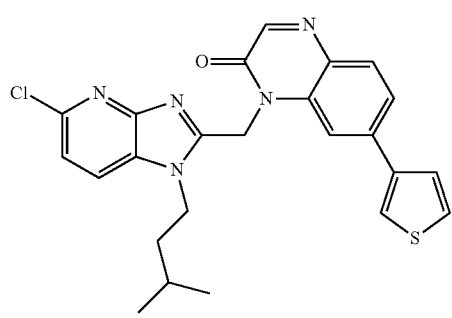 [SMILES: CC(C)CCn1c(Cn2c(=O)cnc3ccc(-c4ccsc4)cc32)nc2nc(Cl)ccc21]

LCMS m/z=464 (M+H)$^+$ $^1$H NMR (400 MHz, CHLOROFORM-d) δ ppm 0.97 (d, J=6.53 Hz, 6H) 1.28-1.48 (m, 2H) 1.63-1.78 (m, 1H) 4.21-4.47 (m, 2H) 5.87 (s, 2H) 7.23 (d, J=8.53 Hz, 1H) 7.48 (dd, J=5.14, 2.89 Hz, 1H) 7.58-7.63 (m, 3H) 7.76 (dd, J=3.01, 1.51 Hz, 1H) 7.86 (d, J=8.28 Hz, 1H) 8.32 (s, 1H) 8.53 (d, J=1.76 Hz, 1H)

tert-butyl 2-(4-((5-chloro-1-isopentyl-1H-imidazo[4,5-b]pyridin-2-yl)methyl)-3-oxo-3,4-dihydroquinoxalin-6-yl)-1H-pyrrole-1-carboxylate P16

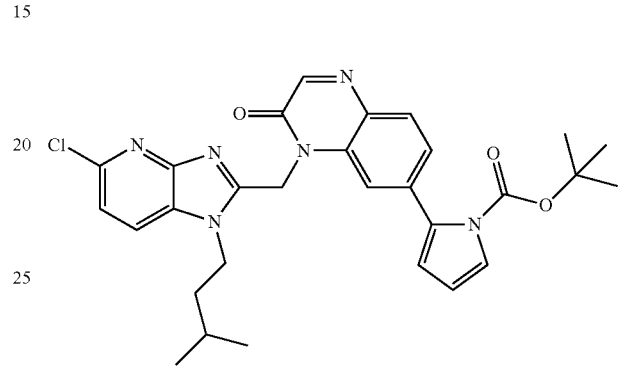

LCMS m/z=547 (M+H)$^+$ $^1$H NMR (400 MHz, CHLOROFORM-d) δ ppm 1.01 (d, J=6.53 Hz, 6H) 1.43 (s, 9H) 1.48-1.55 (m, 2H) 1.67-1.76 (m, 1H) 4.35-4.44 (m, 2H) 5.78 (s, 2H) 6.29 (t, J=3.26 Hz, 1H) 6.40 (dd, J=3.26, 1.76 Hz, 1H) 7.23 (d, J=8.28 Hz, 1H) 7.34-7.38 (m, 2H) 7.61 (d, J=8.28 Hz, 1H) 7.83 (d, J=8.28 Hz, 1H) 8.11 (d, J=1.51 Hz, 1H) 8.33 (s, 1H)

1-((5-chloro-1-isopentyl-1H-imidazo[4,5-b]pyridin-2-yl)methyl)-7-(pyrimidin-5-yl)quinoxalin-2(1H)-one P17

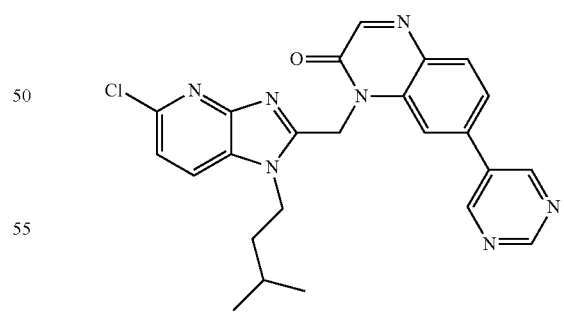

LCMS m/z=460 (M+H)$^+$ $^1$H NMR (400 MHz, CHLOROFORM-d) δ ppm 1.04 (d, J=6.53 Hz, 6H) 1.55-1.67 (m, 2H) 1.70-1.81 (m, 1H) 4.40-4.51 (m, 2H) 5.81 (s, 2H) 7.24 (d, J=8.28 Hz, 1H) 7.59 (dd, J=8.28, 2.01 Hz, 1H) 7.62 (d, J=8.28 Hz, 1H) 8.02 (d, J=8.28 Hz, 1H) 8.38 (s, 1H) 8.40 (d, J=1.76 Hz, 1H) 9.10 (s, 2H) 9.29 (s, 1H)

1-((5-chloro-1-isopentyl-1H-imidazo[4,5-b]pyridin-2-yl)methyl)-7-(4-fluorophenyl)quinoxalin-2(1H)-one P18

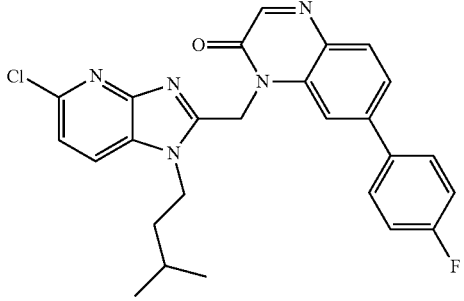 [SMILES: CC(C)CCn1c(Cn2c(=O)cnc3ccc(-c4ccc(F)cc4)cc32)nc2nc(Cl)ccc21]

LCMS m/z=476 (M+H)$^+$ $^1$H NMR (400 MHz, CHLOROFORM-d) δ ppm 1.01 (d, J=6.53 Hz, 6H) 1.45-1.54 (m, 2H) 1.67-1.77 (m, 1H) 4.36-4.46 (m, 2H) 5.85 (s, 2H) 7.19-7.26 (m, 3H) 7.57 (dd, J=8.28, 1.76 Hz, 1H) 7.61 (d, J=8.28 Hz, 1H) 7.70-7.75 (m, 2H) 7.92 (d, J=8.28 Hz, 1H) 8.34 (s, 1H) 8.40 (d, J=1.76 Hz, 1H).

Compounds P19 and P20 were prepared by an analogous reaction protocol as compound P9 and P10 using intermediate 20 and the mixture of (7-fluoroquinoxalin-2(1H)-one 6 and 6-fluoroquinoxalin-2(1H)-one 7) as starting material.

1-((5-chloro-1-isopentyl-1H-imidazo[4,5-b]pyridin-2-yl)methyl)-7-fluoroquinoxalin-2(1H)-one P19

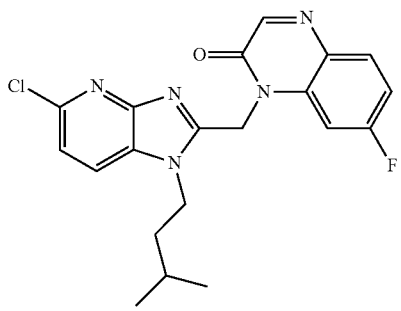 [SMILES: CC(C)CCn1c(Cn2c(=O)cnc3ccc(F)cc32)nc2nc(Cl)ccc21]

LCMS m/z=400 (M+H)$^+$ $^1$H NMR (400 MHz, CHLOROFORM-d) δ ppm 1.01 (d, J=6.8 Hz, 6H), 1.50-1.60 (m, 2H), 1.73 (m, J=6.5 Hz, 1H), 4.36-4.47 (m, 2H), 5.70 (s, 2H), 7.04-7.12 (m, 1H), 7.23 (d, J=8.3 Hz, 1H), 7.62 (d, J=8.3 Hz, 1H), 7.82-7.90 (m, 2H), 8.27 (s, 1H)

1-((5-chloro-1-isopentyl-1H-imidazo[4,5-b]pyridin-2-yl)methyl)-6-fluoroquinoxalin-2(1H)-one P20

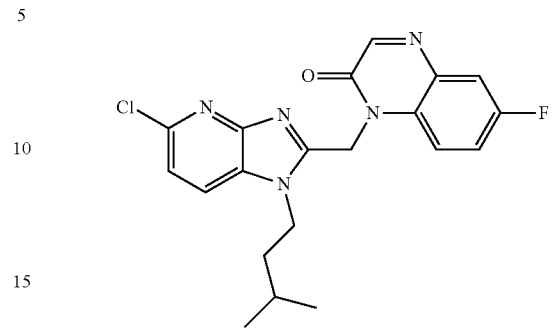

LCMS m/z=400 (M+H)$^+$ $^1$H NMR (400 MHz, CHLOROFORM-d) δ ppm 1.00 (d, J=6.8 Hz, 5H), 1.44-1.54 (m, 2H), 1.65-1.77 (m, 1H), 4.37-4.46 (m, 2H), 5.78 (s, 2H), 7.24 (d, J=8.3 Hz, 1H), 7.35 (m, J=1.5 Hz, 1H), 7.56 (dd, J=8.3, 3.0 Hz, 1H), 7.61 (d, J=8.3 Hz, 1H), 8.26 (dd, J=9.4, 4.6 Hz, 1H), 8.37 (s, 1H)

1-((5-chloro-1-isopentyl-1H-imidazo[4,5-b]pyridin-2-yl)methyl)pyrido[4,3-b]pyrazin-2(1H)-one P21

Compound P21 was prepared by an analogous reaction protocol as compound P9 using intermediate 20 and pyrido[4,3-b]pyrazin-2(1H)-one 10 as starting material.

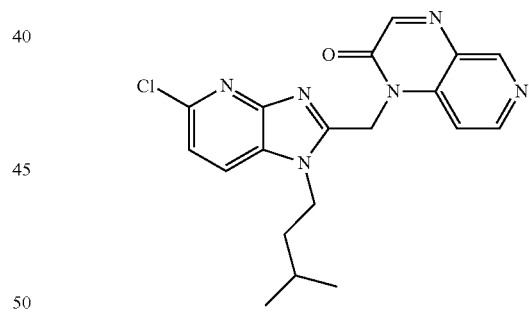

LCMS m/z=483 (M+H)$^+$ $^1$H NMR (400 MHz, DMSO-d$_6$) δ ppm 1.00 (d, J=5.5 Hz, 6H), 1.64-1.84 (m, 3H), 4.36-4.55 (m, 2H), 5.79 (s, 2H), 7.35 (d, J=8.3 Hz, 1H), 7.68 (d, J=5.8 Hz, 1H), 8.17 (d, J=8.5 Hz, 1H), 8.44 (s, 1H), 8.63 (d, J=5.8 Hz, 1H), 9.07 (s, 1H)

4-((5-chloro-1-isopentyl-1H-imidazo[4,5-b]pyridin-2-yl)methyl)-1-cyclopropyl-1,2-dihydropyrido[3,4-b]pyrazin-3(4H)-one P22

Compound P22 was prepared by an analogous reaction protocol as compound P9 using intermediate 20 and ethyl 1-cyclopropyl-1,2-dihydropyrido[4,3-b]pyrazin-3(4H)-one 4 as starting material.

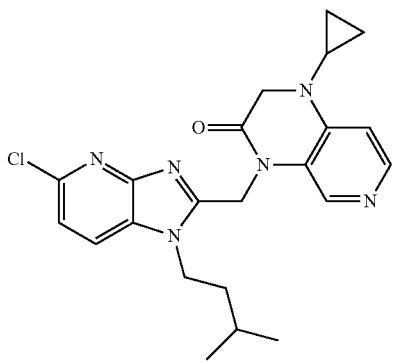 [SMILES: CC(C)CCn1c(CN2C(=O)CN(C3CC3)c3ccncc32)nc2nc(Cl)ccc21]

LCMS m/z=424 (M+H)+

¹H NMR (400 MHz, CHLOROFORM-d) δ ppm 0.66 (m, J=3.5, 1.8 Hz, 2H), 0.94 (m, J=6.5, 1.5 Hz, 2H), 1.01 (d, J=6.5 Hz, 6H), 1.61-1.76 (m, 3H), 2.35-2.42 (m, 1H), 4.03 (s, 2H), 4.23-4.31 (m, 2H), 5.41 (s, 2H), 7.03 (d, J=5.5 Hz, 1H), 7.20 (d, J=8.3 Hz, 1H), 7.58 (d, J=8.3 Hz, 1H), 8.15 (d, J=5.3 Hz, 1H), 8.40 (s, 1H)

Synthesis of 4-((5-bromo-1-(3-(methylsulfonyl)propyl)-1H-benzo[d]imidazol-2-yl)methyl)-1-cyclopropyl-1,2-dihydropyrido[3,4-b]pyrazin-3(4H)-one P23

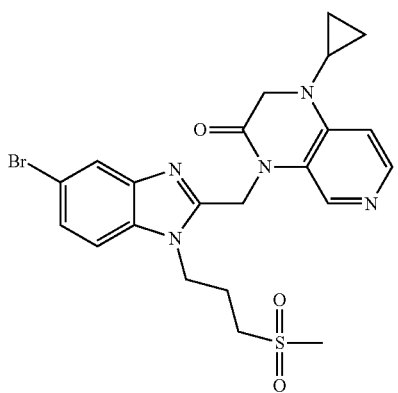

Synthesis of intermediate 3-(methylsulfonyl)propan-1-amine hydrochloride 25

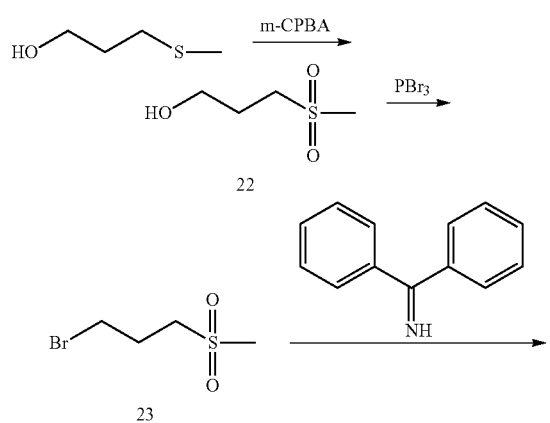

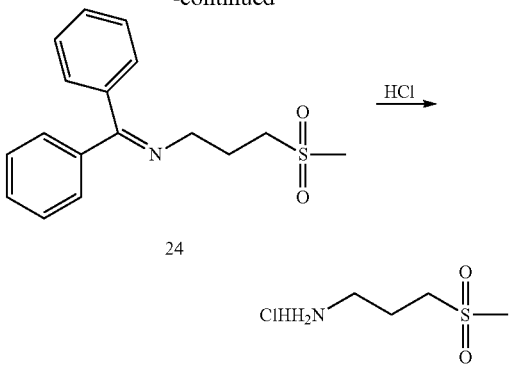

Step 1: Synthesis of 3-(methylsulfonyl)propan-1-ol 22

The 3-(methylthio)propan-1-ol (200 g, 1900 mmol, CAS 505-10-2) was dissolved in CH₂Cl₂ (2000 mL). The mixture was cooled to 0° C. The m-CPBA 85% in water (970 g, 5700 mmol, CAS 937-14-4) was added portion wise keeping the temperature between 0 and 5° C. After addition, the mixture was allowed to warm to 25° C. and stirred for 15 h. The mixture was filtered through a celite pad. The filtrate was purified by flash column (Eluent: petroleum ether:ethyl acetate=3:1 and then ethyl acetate:methanol=10:1) to yield the intermediate 22 (75 g, 29%).

Step 2: Synthesis of 1-bromo-3-(methylsulfonyl)propane 23

The intermediate 22 (75 g, 543 mmol) was dissolved in CH₂Cl₂ (750 mL). The mixture was cooled to 0° C. The phosphorus tribromide (53.6 mL, 570 mmol) was added dropwise keeping the temperature between 0 and 5° C. After addition, the mixture was allowed to warm to 25° C. and stirred for 15 h. The mixture was poured into ice-water. The separated organic layer was washed with brine (2×500 mL), dried over Na₂SO₄, filtered and evaporated under vacuum to yield the title compound 23 (77 g, 71%).

¹H NMR (400 MHz, CHLOROFORM-d) δ ppm 2.25-2.40 (m, 2H) 2.91 (s, 3H) 3.1-3.2 (m, 2H) 3.5-3.6 (m, 2H).

Step 3: Synthesis of N-(diphenylmethylene)-3-(methylsulfonyl)propan-amines 24

The intermediate 23 (27 g, 134 mmol) was dissolved in CH₃CN (60 mL). Diphenylmethanimine (27 g, 148 mmol) and DIEA (19.6 g, 152 mmol) were added. The mixture was refluxed for 4 h and then cooled to room temperature. The mixture was neutralized with 50% aqueous acetic acid at 25° C. Water (80 mL) was added. The mixture was extracted with ethyl acetate (2×300 mL). The combined organic layers were washed with brine, dried over Na₂SO₄, filtered and evaporated under vacuum. The residue was washed with petroleum ether (4×100 mL). The mixture was treated with methyl tert-butyl ether. The solid was collected and washed with petroleum ether. The filtrate was dried under vacuum. The residue was purified by column chromatography (Eluent: CH₂Cl₂:ethyl acetate from 1:0 to 10:1). The title compound 24 was obtained as a white solid (34 g, 85%).

Step 4: Synthesis of 3-(methylsulfonyl)propan-1-amine hydrochloride 25

The intermediate 24 (34 g, 113 mmol) was dissolved in dioxane (600 mL). The mixture was cooled to 0-5° C. and a solution of 4N HCl/dioxane (120 mL, 480 mmol) was added dropwise. After addition, the mixture was allowed to warm to 25° C. and stirred for 15 h. The mixture was filtered. The solid was collected and washed with dioxane. The title product 25 was obtained as a yellow powder (11.5 g, 50%).

Step 5: Synthesis of 4-bromo-N-(3-(methylsulfonyl)propyl)-2-nitroaniline 27

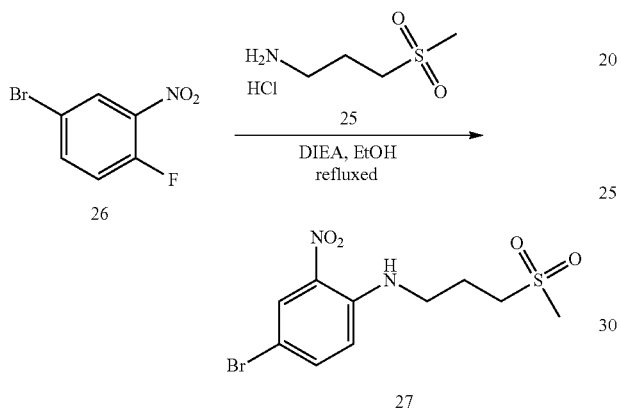

The mixture of 4-bromo-1-fluoro-2-nitrobenzene 26 (7.6 g, 35 mmol), 3-(methylsulfonyl) propan-1-amine hydrochloride 25 (6 g, 35 mmol) and diisopropylethylamine (DIEA) (13.5 g, 105 mmol) were dissolved in ethanol (70 mL) and refluxed for 14 h. The reaction mixture was cooled to 20° C. The precipitate was filtered and washed with ethanol. 11 g (94%) of intermediate 27 was obtained as an orange powder.

LCMS m/z=337 (M+H)⁺

Step 6: Synthesis of 4-bromo-N¹-(3-(methylsulfonyl)propyl)benzene-1,2-diamine 28

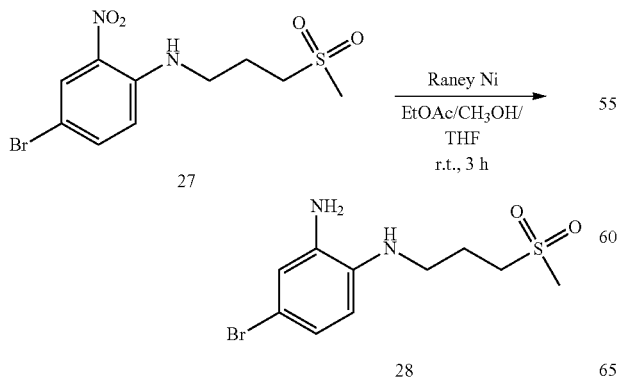

Intermediate 27 (10 g, 29.7 mmol) in methanol (200 mL), EtOAc (200 mL) and THF (200 mL) was hydrogenated with Raney Ni (10 g) as a catalyst at 20° C. (1 atm) for 3 h. After uptake of H₂ (3 eq), the catalyst was filtered off and the filtrate was evaporated. 10 g (90%) of compound 28 was obtained as a black solid.

LCMS m/z=307 (M+H)⁺

Step 7: 5-bromo-2-(diethoxymethyl)-1-(3-(methylsulfonyl)propyl)-1H-benzo[d]imidazole 29

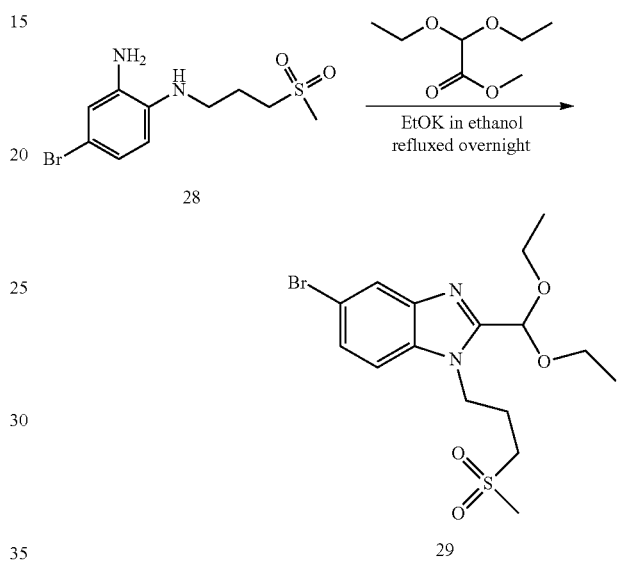

Intermediate 28 (10 g, 29.7 mmol) and methyl diethoxy-acetate (9.2 g, 68.31 mmol) in 24 wt % potassiumethanolate in ethanol (13.5 g, 38.5 mmol) were stirred and refluxed overnight. The mixture was evaporated under vacuum. Water (200 mL) was added. Acetic acid was added to neutralize the mixture. The mixture was extracted with ethyl acetate (2×100 mL). The combined organic layers were washed with saturated NaHCO₃, brine and dried over Na₂SO₄. The solvent was removed under vacuum to yield 12.3 g (90%) of compound 29 as dark oil.

LCMS m/z=419 (M+H)⁺

Step 8: Synthesis of (5-bromo-1-(3-(methylsulfonyl)propyl)-1H-benzo[d]imidazol-2-yl)methanol 30

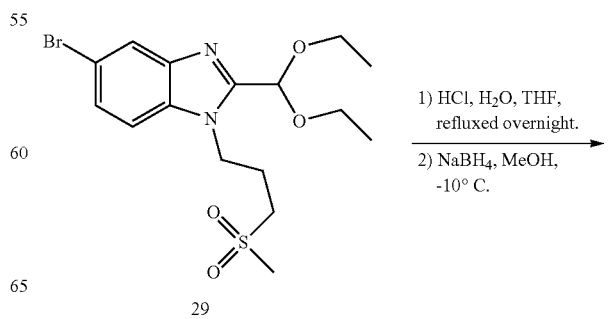

-continued

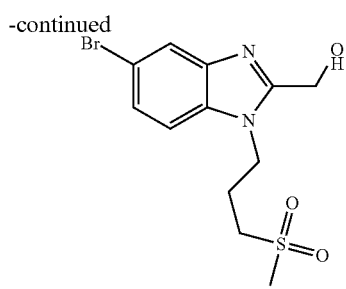

30

Intermediate 29 (12.3 g, 29.3 mmol) in THF (100 mL) was stirred for 0.5 h at 20° C. to dissolve. Conc. HCl (21 mL) and H$_2$O (42 mL) were added. The mixture was refluxed for 6 h and then cooled to −10° C. CH$_3$OH (50 mL) were added, followed by careful addition of NaBH$_4$ (24 g, 629 mmol). The mixture was stirred for 0.5 h at 10° C. and concentrated under vacuum. Water (200 mL) was added. The mixture was extracted with ethyl acetate (2×100 mL). The combined organic layers were washed with brine and dried over Na$_2$SO$_4$. The solvent was removed under vacuum. The resulting solid was washed with ethyl acetate (2×5 mL) and dried under vacuum. 6.8 g (60%) of intermediate 30 was obtained as an off-white solid.

LCMS m/z=347 (M+H)$^+$ $^1$H NMR (400 MHz, DMSO-d$_6$) δ ppm 2.20 (dq, J=7.8, 7.5 Hz, 2H), 2.98 (s, 3H), 3.16-3.24 (m, 2H), 4.42 (t, J=7.4 Hz, 2H), 4.73 (d, J=6.0 Hz, 2H), 5.73 (t, J=5.8 Hz, 1H), 7.42 (dd, J=8.7, 1.9 Hz, 1H), 7.63 (d, J=8.5 Hz, 1H), 7.79-7.83 (m, 1H)

Step 9: Synthesis of 5-bromo-2-(chloromethyl)-1-(3-(methylsulfonyl)propyl)-1H-benzo[d]imidazole hydrochloride 31

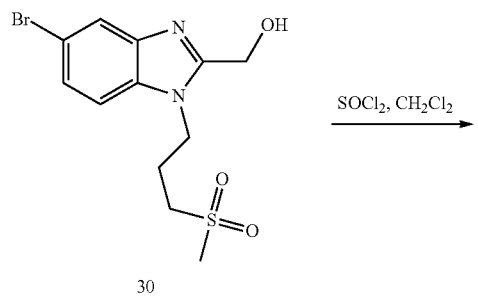

To a solution of alcohol 30 (363 mg, 1.414 mmole) in 30 mL of dichloromethane was added dropwise a solution of thionyl chloride (336 mg, 2 eq) in 10 mL of dichloromethane. The reaction mixture was stirred for one hour at 45° C. It was then concentrated under vacuum to give the desired intermediate 31 (440 mg, 99%) as an HCl salt, which was used as such in the next step.

Step 10: Synthesis of 4-((5-bromo-1-(3-(methylsulfonyl)propyl)-1H-benzo[d]imidazol-2-yl)methyl)-1-cyclopropyl-1,2-dihydropyrido[3,4-b]pyrazin-3(4H)-one P23

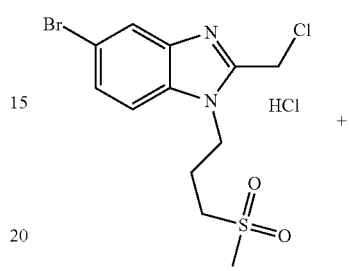

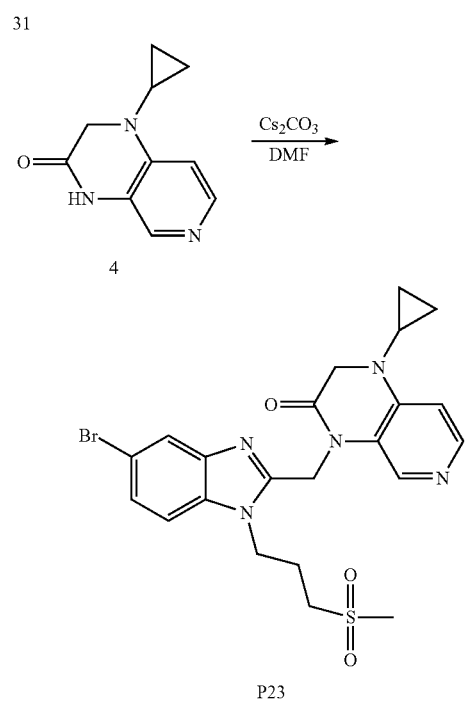

5-bromo-2-(chloromethyl)-1-[3-(methylsulfonyl)propyl]-H-benzimidazole acid chloride salt 31 (500 mg, 1.2 mmol) was dissolved in 20 ml DMF at room temperature. 1-cyclopropyl-1,4-dihydropyrido[3,4-b]pyrazin-3(2H)-one 4 (235 mg, 1.2 mmol, 1 eq.) and Cs$_2$CO$_3$ (1.2 g, 3.7 mmol, 3 eq.) were added to the solution. The reaction mixture was stirred at room temperature for 16 hours. The reaction mixture was then diluted with water and extracted with ethylacetate. The combined organics were dried over MgSO$_4$, evaporated and purified by Prep. HPLC on (RP Vydac Denali C18-10 μm, 200 g, 5 cm) using a 0.25% NH$_4$HCO$_3$ in water-CH$_3$CN solution as eluent. After evaporation and drying in vacuo 4-((5-bromo-1-(3-(methylsulfonyl)propyl)-1H-benzo[d]imidazol-2-yl)methyl)-1-cyclopropyl-1,2-dihydropyrido[3,4-b]pyrazin-3(4H)-one P23 (184 mg, 28%) was obtained.

LCMS m/z=518 (M+H)$^+$ $^1$H NMR (400 MHz, DMSO-d$_6$) δ ppm 0.52-0.73 (m, 2H) 0.81-0.96 (m, 2H) 2.19 (quin, J=7.47 Hz, 2H) 2.42-2.48 (m, 1H) 3.00 (s, 3H) 3.19-3.29 (m, 2H) 4.05 (s, 2H) 4.46 (t, J=7.40 Hz, 2H) 5.44 (s, 2H) 7.09 (d, J=5.27 Hz, 1H) 7.41 (dd, J=8.53, 1.76 Hz, 1H) 7.63 (d, J=8.53 Hz, 1H) 7.77 (d, J=2.01 Hz, 1H) 8.07 (d, J=5.52 Hz, 1H) 8.21 (s, 1H)

Synthesis of 1-((5-bromo-1-(3-(methylsulfonyl)propyl)-1H-benzo[d]imidazol-2-yl)-methyl)-7-fluoroquinoxalin-2(1H)-one P24 and 1-((5-bromo-1-(3-(methylsulfonyl)-propyl)-1H-benzo[d]imidazol-2-yl)methyl)-6-fluoroquinoxalin-2(1H)-one P25

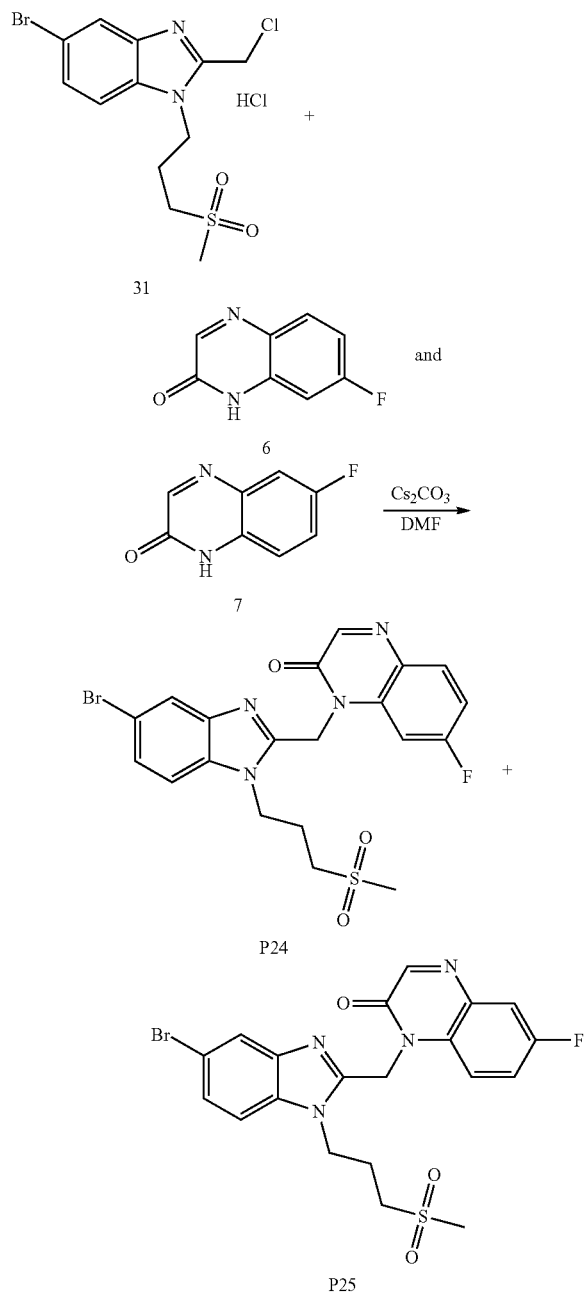

5-bromo-2-(chloromethyl)-1-[3-(methylsulfonyl)propyl]-1H-benzimidazole acid chloride salt 31 (300 mg, 0.75 mmol) was dissolved in 20 ml DMF at room temperature. A mixture of 7-fluoroquinoxalin-2(1H)-one 6 and 6-fluoroquinoxalin-2(1H)-one 7 (ratio: 1/1) (123 mg, 0.75 mmol, 1 eq.) and $Cs_2CO_3$ (13 g, 40 mmol, 3 eq.) were added to the solution. The reaction mixture was stirred at room temperature for 16 hours. The reaction mixture was then diluted with water and extracted with ethylacetate. The combined organics were dried over MgSO4 and evaporated. The resulting residue was purified by Prep. HPLC on (RP Vydac Denali C18-10 µm, 200 g, 5 cm), using a 0.25% $NH_4HCO_3$ in water-$CH_3CN$ solution as eluent. After evaporation and drying in vacuo 44 mg of P24 (12%) and 44 mg (12%) P25 were obtained separately.

1-((5-bromo-1-(3-(methylsulfonyl)propyl)-1H-benzo[d]imidazol-2-yl)methyl)-7-fluoroquinoxalin-2(1H)-one P24

LCMS m/z=493 (M+H)+

$^1$H NMR (400 MHz, CHLOROFORM-d) δ ppm 2.27-2.40 (m, 2H) 3.00 (s, 3H) 3.16 (t, J=6.90 Hz, 2H) 4.50-4.63 (m, 2H) 5.68 (s, 2H) 7.11 (dd, J=2.51, 1.00 Hz, 1H) 7.29 (d, J=8.78 Hz, 1H) 7.42 (dd, J=8.78, 1.76 Hz, 1H) 7.82-7.91 (m, 3H) 8.28 (s, 1H)

1-((5-bromo-1-(3-(methylsulfonyl)propyl)-1H-benzo[d]imidazol-2-yl)methyl)-6-fluoroquinoxalin-2(1H)-one P25

LCMS m/z=493 (M+H)+

$^1$H NMR (400 MHz, CHLOROFORM-d) δ ppm 2.22-2.39 (m, 2H) 2.99 (s, 3H) 3.16 (t, J=7.03 Hz, 2H) 4.51-4.64 (m, 2H) 5.73 (s, 2H) 7.29 (d, J=8.78 Hz, 1H) 7.34-7.45 (m, 2H) 7.60 (dd, J=8.41, 2.89 Hz, 1H) 7.87 (d, J=1.76 Hz, 1H) 8.14 (dd, J=9.41, 4.64 Hz, 1H) 8.37 (s, 1H)

Synthesis of 4-((5-chloro-1-(3-(methylsulfonyl)propyl)-1H-benzo[d]imidazol-2-yl)-methyl)-1-cyclopropyl-1,2-dihydropyrido[3,4-b]pyrazin-3(4H)-one P26

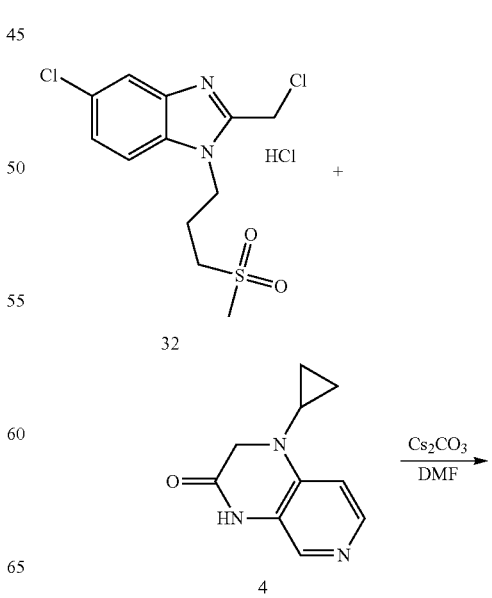

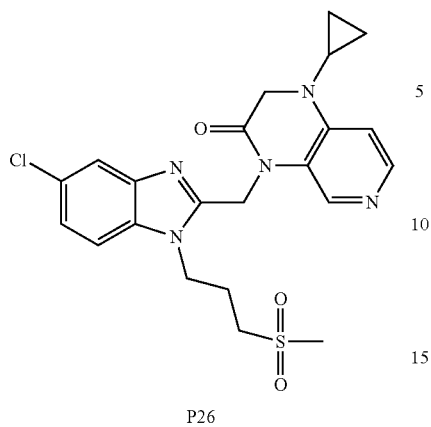

P26

Compound P26 was prepared by an analogous reaction protocol as compound P23 using intermediate 32 and ethyl 1-cyclopropyl-1,2-dihydropyrido[4,3-b]pyrazin-3(4H)-one 4 as starting material.

LCMS m/z=475 (M+H)$^+$ $^1$H NMR (400 MHz, DMSO-d$_6$) δ ppm 0.59-0.68 (m, 2H), 0.84-0.93 (m, 2H), 2.13-2.25 (m, 2H), 2.43-2.48 (m, 1H), 3.01 (s, 3H), 3.21-3.28 (m, 2H), 4.05 (s, 2H), 4.47 (t, J=7.4 Hz, 2H), 5.44 (s, 2H), 7.10 (d, J=5.5 Hz, 1H), 7.30 (dd, J=8.5, 2.0 Hz, 1H), 7.63 (d, J=2.0 Hz, 1H), 7.67 (d, J=8.5 Hz, 1H), 8.07 (d, J=5.5 Hz, 1H), 8.22 (s, 1H)

Synthesis of 4-((5-chloro-1-(4,4,4-trifluorobutyl)-1H-benzo[d]imidazol-2-yl)methyl)-1-cyclopropyl-1,2-dihydropyrido[3,4-b]pyrazin-3(4H)-one P27

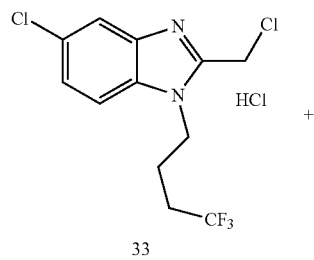

33

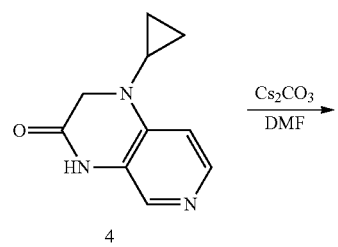

4

→ Cs$_2$CO$_3$ / DMF

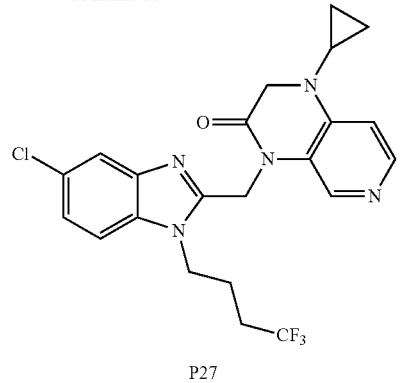

P27

Compound P27 was prepared by an analogous reaction protocol as compound P23 using intermediate 33 and ethyl 1-cyclopropyl-1,2-dihydropyrido[4,3-b]pyrazin-3 (4H)-one 4 as starting material.

LCMS m/z=464 (M+H)$^+$ $^1$H NMR (400 MHz, DMSO-d$_6$) δ ppm 0.56-0.65 (m, 2H), 0.84-0.94 (m, 2H), 1.97 (t, J=7.8 Hz, 2H), 2.31-2.45 (m, 3H), 4.04 (s, 2H), 4.41 (t, J=7.5 Hz, 2H), 5.44 (s, 2H), 7.10 (d, J=5.5 Hz, 1H), 7.29 (dd, J=8.5, 2.0 Hz, 1H), 7.63 (d, J=1.8 Hz, 1H), 7.68 (d, J=8.5 Hz, 1H), 8.07 (d, J=5.5 Hz, 1H), 8.23 (s, 1H)

Synthesis of 1-((5-bromo-1-(3-(methylsulfonyl)propyl)-1H-indol-2-yl)methyl)-7-fluoroquinoxalin-2 (1H)-one P28 and 1-((5-bromo-1-(3-(methylsulfonyl)propyl)-1H-indol-2-yl)methyl)-6-fluoroquinoxalin-2(1H)-one P29

Step 1: Synthesis of ethyl 5-bromo-1-(3-(methylsulfonyl)propyl)-1H-indole-2-carboxylate P34

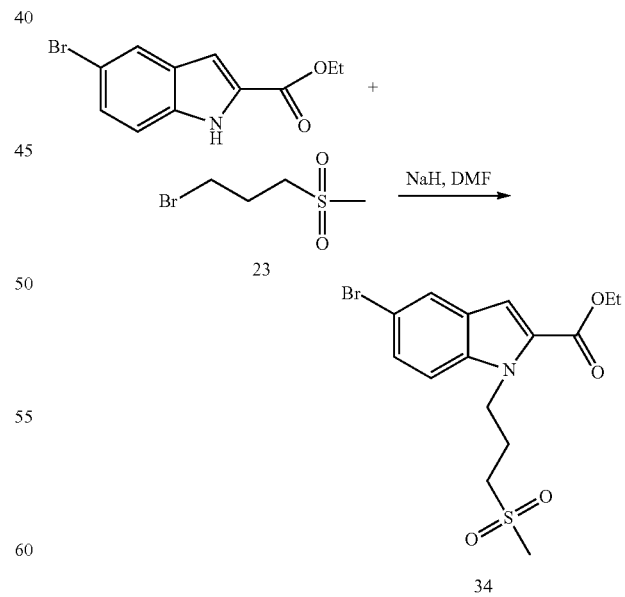

Ethyl 5-bromo-1H-indole-2-carboxylate (CAS 16732-70-0) (2.3 g, 8.6 mmol) was dissolved in DMF (50 mL). The mixture was stirred at room temperature, then sodium hydride 60% suspension in mineral oil (0.52 g, 12.8 mmol)

was added. The resulting mixture was stirred at room temperature for 1 hour, then 1-bromo-3-(methylsulfonyl)-propane 23 (2.6 g, 12.8 mmol) was added. The resulting mixture was stirred at room temperature overnight. The mixture was poured in ice/water solution and extracted with ethyl acetate. The organic layer was dried over MgSO₄ and concentrated to yield a brown crude oil. The crude was purified by column chromatography using dichloromethane/methanol to yield the title intermediate 34 (3.2 g, 96%) as a white solid.

m/z=389 (M+H)⁺.

Step 2: Synthesis of (5-bromo-1-(3-(methylsulfonyl)propyl)-1H-indol-2-yl)methanol 35

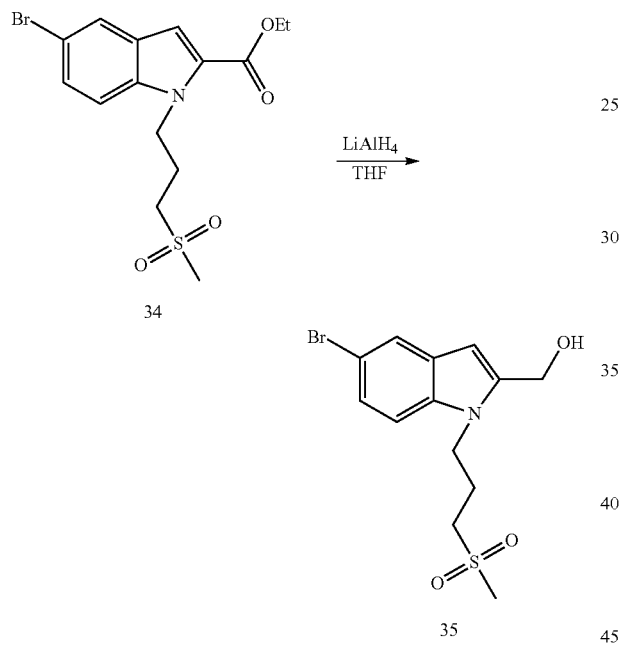

To a solution of intermediate 34 (3.2 g, 8.24 mmol) in THF (100 mL) was added at room temperature lithium aluminum hydride (2 M solution in THF, 5.2 mL, 10.4 mmol). The resulting mixture was stirred at room temperature overnight. The reaction mixture was quenched by addition of ethyl acetate and ethanol. The resulting mixture was poured in ice/water solution then filtered on celite. The aqueous layer was extracted with ethyl acetate (3×50 mL). The combined organic extracts were washed with brine (100 mL), dried over MgSO₄, filtered and concentrated under reduced pressure. The residue was purified by column chromatography using dichloromethane/methanol as the eluent. The intermediate 35 was collected (2.5 g, 88%) as a white solid.

m/z=347 (M+H)⁺.

Step 3: Synthesis of 1-((5-bromo-1-(3-(methylsulfonyl)propyl)-1H-indol-2-yl)methyl)-7-fluoroquinoxalin-2(1H)-one P28 and 1-((5-bromo-1-(3-(methylsulfonyl)propyl)-1H-indol-2-yl)methyl)-6-fluoroquinoxalin-2(1H)-one P29

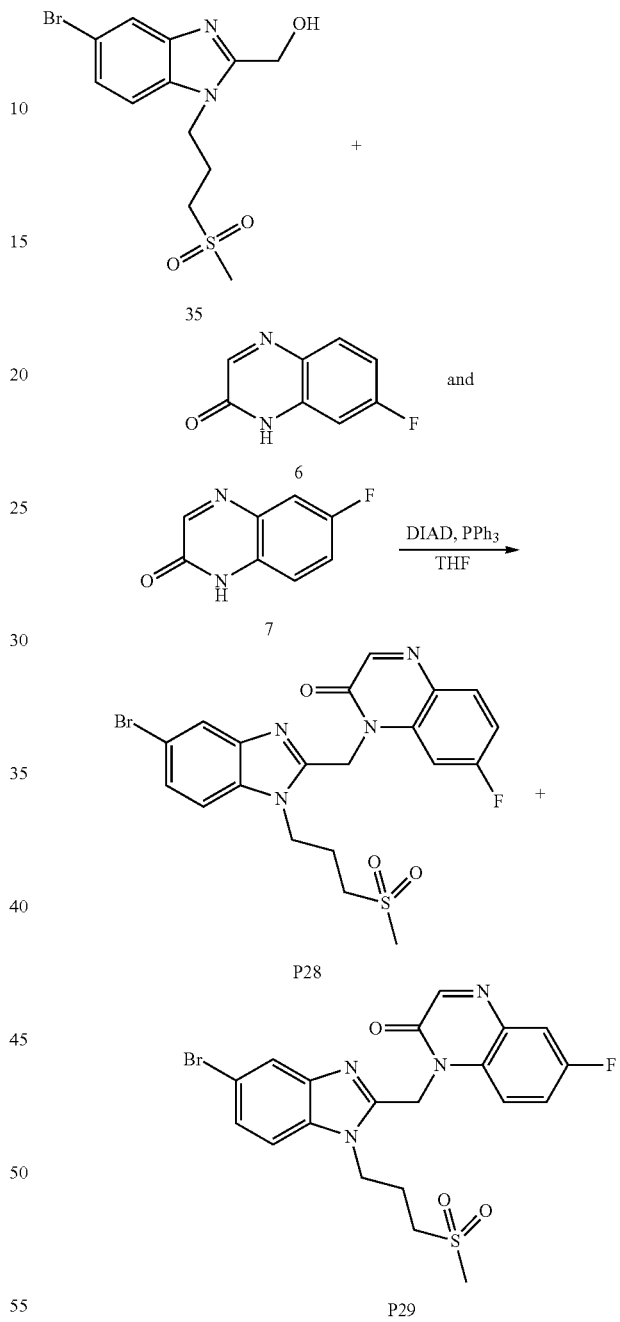

To a stirred solution of intermediate 35 (1 g, 2.7 mmol), triphenyl phosphine (0.87 g, 3.3 mmol) and the mixture of intermediate 6 and 7 (0.546 g, 3.3 mmol) in dry THF (100 mL) was added DIAD (94%, 0.8 mL, 4.16 mmol) dropwise at room temperature. The reaction mixture was stirred overnight. After the completion of reaction, the mixture was concentrated to dryness and the residue was purified by column chromatography eluted with ethyl acetate/heptane then ethyl acetate the mixture of isomers was separated by SFC.

1-((5-bromo-1-(3-(methylsulfonyl)propyl)-1H-indol-2-yl)methyl)-7-fluoroquinoxalin-2(1H)-one P28

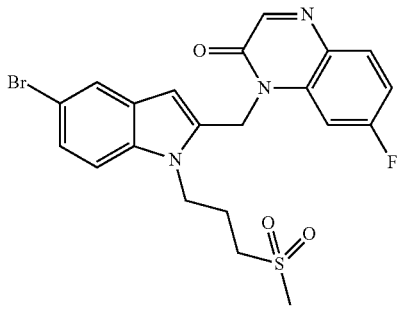 [SMILES: CS(=O)(=O)CCCn1c(Cn2c(=O)cnc3ccc(F)cc32)cc2cc(Br)ccc21]

LCMS m/z=493 (M+H)+
$^1$H NMR (400 MHz, DMSO-d6) δ ppm 2.18 (quin, J=7.6 Hz, 2H), 3.02 (s, 3H), 3.23-3.29 (m, 2H), 4.45 (t, J=7.6 Hz, 2H), 5.64 (s, 2H), 5.91 (s, 1H), 7.26 (dd, J=8.7, 2.0 Hz, 1H), 7.29 (td, J=8.6, 2.6 Hz, 1H), 7.51 (dd, J=10.9, 2.6 Hz, 1H), 7.54 (d, J=8.8 Hz, 1H), 7.75 (d, J=1.9 Hz, 1H), 7.97 (dd, J=8.9, 6.1 Hz, 1H), 8.32 (s, 1H)

1-((5-bromo-1-(3-(methylsulfonyl)propyl)-1H-indol-2-yl)methyl)-6-fluoroquinoxalin-2(1H)-one P29

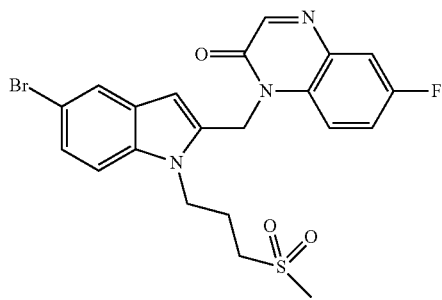 [SMILES: CS(=O)(=O)CCCn1c(Cn2c(=O)cnc3cc(F)ccc32)cc2cc(Br)ccc21]

LCMS m/z=493 (M+H)+
$^1$H NMR (400 MHz, DMSO-d6) δ ppm 2.18 (quin, J=7.6 Hz, 2H), 3.03 (s, 3H), 3.23-3.29 (m, 2H), 4.46 (t, J=7.6 Hz, 2H), 5.68 (s, 2H), 5.91 (s, 1H), 7.26 (dd, J=8.7, 2.0 Hz, 1H), 7.50-7.54 (m, 1H), 7.54 (d, J=8.8 Hz, 1H), 7.56 (d, J=1.8 Hz, 1H), 7.59 (dd, J=9.4, 4.8 Hz, 1H), 7.77 (dd, J=8.9, 2.9 Hz, 1H), 8.42 (s, 1H)

Antiviral Activity

Black 96-well clear-bottom microtiter plates (Corning, Amsterdam, The Netherlands) were filled in duplicate using a customized robot system with serial 4-fold dilutions of compound in a final volume of 50 µl culture medium [RPMI medium without phenol red, 10% FBS, 0.04% gentamycin (50 mg/ml) and 0.5% DMSO]. Then, 100 µl of a HeLa cell suspension (5×10$^4$ cells/ml) in culture medium was added to each well followed by the addition of 50 µl rgRSV224 (MOI=0.02) virus in culture medium using a multidrop dispenser (Thermo Scientific, Erembodegem, Belgium). rgRSV224 virus is an engineered virus that includes an additional GFP gene (Hallak et al, 2000) and was in-licensed from the NIH (Bethesda, Md., USA). Medium, virus- and mock-infected controls were included in each test. Cells were incubated at 37° C. in a 5% CO$_2$ atmosphere. Three days post-virus exposure, viral replication was quantified by measuring GFP expression in the cells by a MSM laser microscope (Tibotec, Beerse, Belgium). The EC$_{50}$ was defined as the 50% inhibitory concentration for GFP expression. In parallel, compounds were incubated for three days in a set of white 96-well microtitier plates (Corning) and the cytotoxicity of compounds in HeLa cells was determined by measuring the ATP content of the cells using the ATPlite kit (PerkinElmer, Zaventem, Belgium) according to the manufacturer's instructions. The CC$_{50}$ was defined as the 50% concentration for cytotoxicity.

| | Structure | WT activity EC$_{50}$ (µM) | Tox CC$_{50}$ (µM) |
|---|---|---|---|
| P1 | 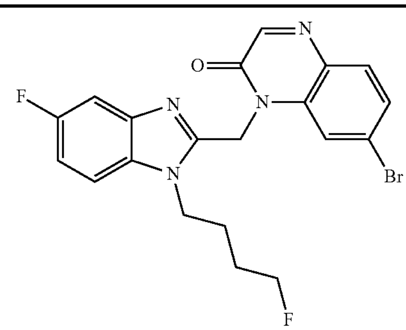 | 0.071 | 87.05 |
| P2 | 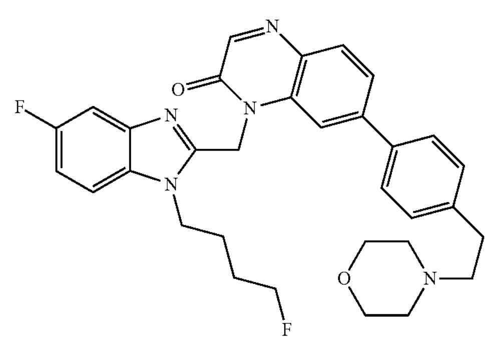 [SMILES: O=c1cnc2ccc(-c3ccc(CCN4CCOCC4)cc3)cc2n1Cc1nc2cc(F)ccc2n1CCCCF] | >10.08 | 93.96 |

-continued

| | Structure | WT activity EC$_{50}$ (μM) | Tox CC$_{50}$ (μM) |
|---|---|---|---|
| P3 | 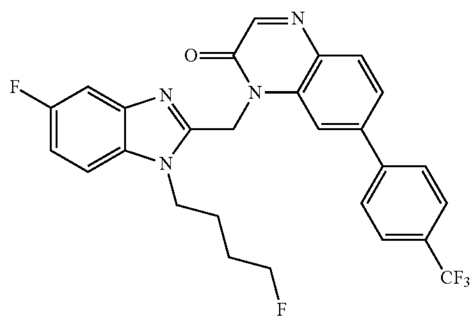 [SMILES: O=c1cnc2ccc(-c3ccc(C(F)(F)F)cc3)cc2n1Cc1nc2cc(F)ccc2n1CCCCF] | >10.08 | 42.39 |
| P4 | 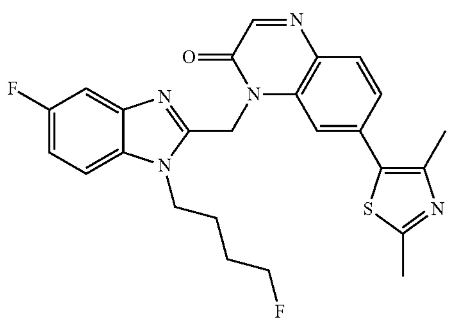 [SMILES: Cc1nc(C)c(-c2ccc3ncc(=O)n(Cc4nc5cc(F)ccc5n4CCCCF)c3c2)s1] | 4.78 | 31.07 |
| P5 | 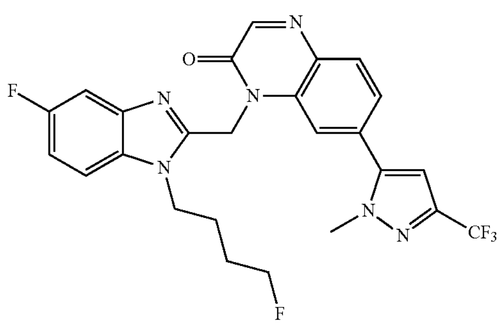 [SMILES: Cn1nc(C(F)(F)F)cc1-c1ccc2ncc(=O)n(Cc3nc4cc(F)ccc4n3CCCCF)c2c1] | 4.89 | 53.26 |
| P6 | 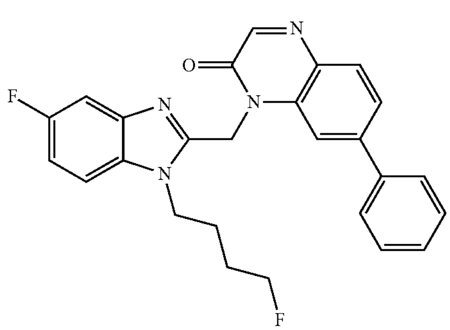 | 3.94 | 42.78 |

-continued

| | Structure | WT activity EC$_{50}$ (μM) | Tox CC$_{50}$ (μM) |
|---|---|---|---|
| P7 | 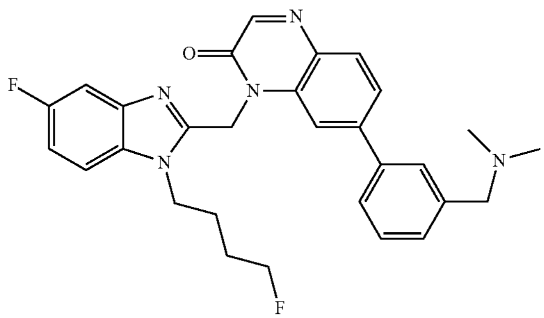 [SMILES: CN(C)Cc1cccc(-c2ccc3ncc(=O)n(Cc4nc5cc(F)ccc5n4CCCCF)c3c2)c1] | 0.099 | 17.56 |
| P8 | 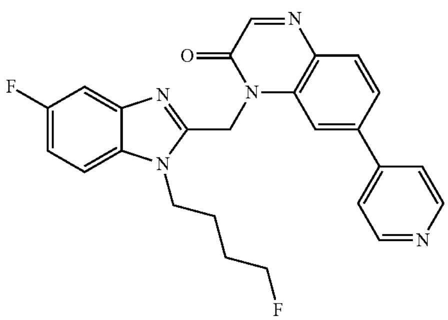 [SMILES: O=c1cnc2ccc(-c3ccncc3)cc2n1Cc1nc2cc(F)ccc2n1CCCCF] | 2.69 | 86.83 |
| P9 | 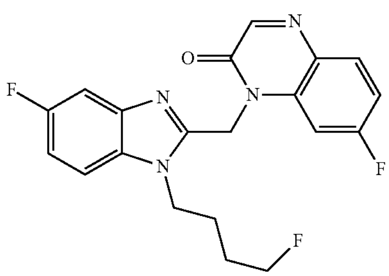 [SMILES: O=c1cnc2ccc(F)cc2n1Cc1nc2cc(F)ccc2n1CCCCF] | 0.27 | >100 |
| P10 | 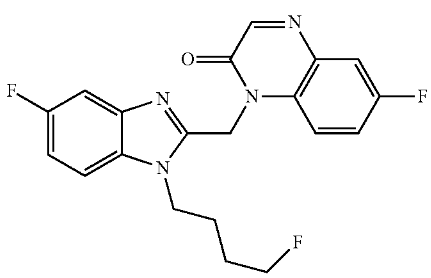 [SMILES: O=c1cnc2cc(F)ccc2n1Cc1nc2cc(F)ccc2n1CCCCF] | 1.04 | >100 |
| P11 | 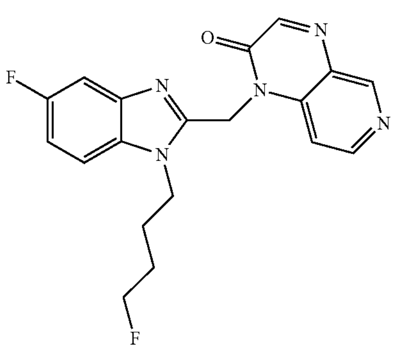 [SMILES: O=c1cnc2cnccc2n1Cc1nc2cc(F)ccc2n1CCCCF] | 7.21 | >100 |

-continued

| | Structure | WT activity EC$_{50}$ (μM) | Tox CC$_{50}$ (μM) |
|---|---|---|---|
| P12 | 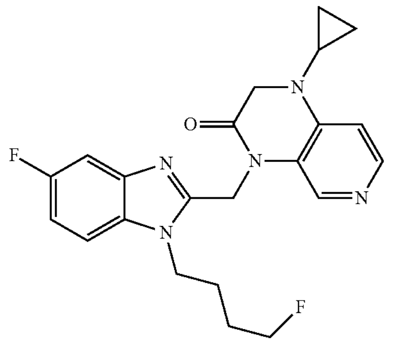 [SMILES: O=C1CN(C2CC2)c2ccncc2N1Cc1nc2cc(F)ccc2n1CCCCF] | 0.011 | 50.11 |
| P13 | 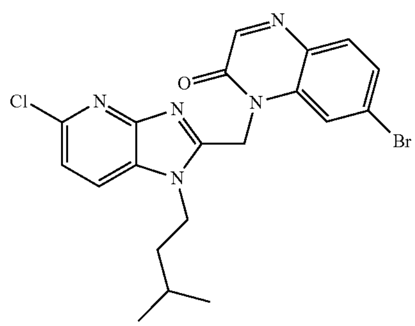 [SMILES: CC(C)CCn1c(Cn2c(=O)cnc3ccc(Br)cc32)nc2nc(Cl)ccc21] | 0.004 | 46.48 |
| P14 | 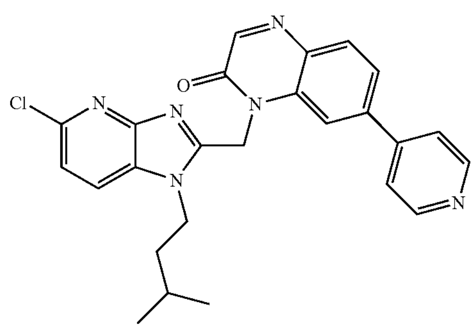 [SMILES: CC(C)CCn1c(Cn2c(=O)cnc3ccc(-c4ccncc4)cc32)nc2nc(Cl)ccc21] | 0.061 | 14.67 |
| P15 | 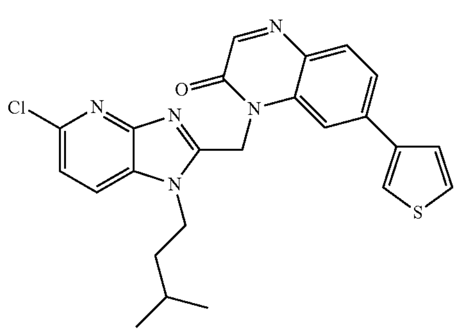 [SMILES: CC(C)CCn1c(Cn2c(=O)cnc3ccc(-c4ccsc4)cc32)nc2nc(Cl)ccc21] | 0.34 | 27.61 |

-continued

| | Structure | WT activity EC$_{50}$ (μM) | Tox CC$_{50}$ (μM) |
|---|---|---|---|
| P16 | 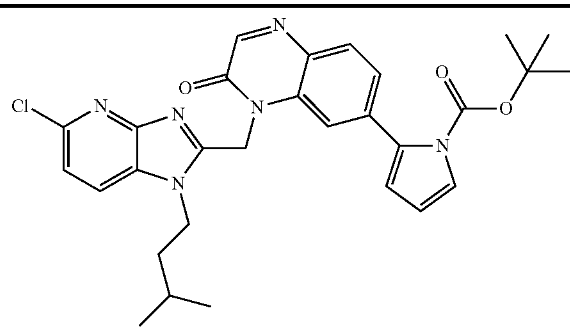 | 0.51 | 42.47 |
| P17 | 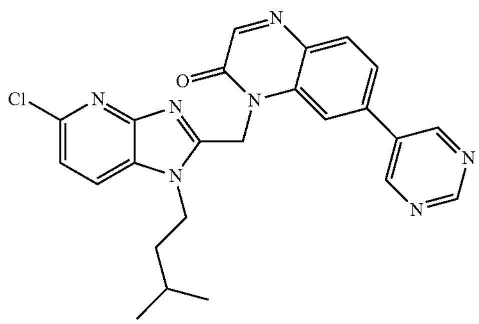 [SMILES: CC(C)CCn1c(Cn2c(=O)cnc3ccc(-c4cncnc4)cc32)nc2nc(Cl)ccc21] | 0.48 | >100 |
| P18 | 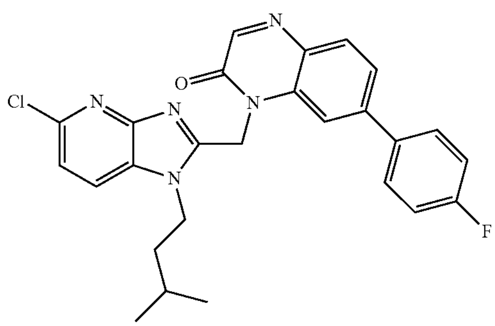 [SMILES: CC(C)CCn1c(Cn2c(=O)cnc3ccc(-c4ccc(F)cc4)cc32)nc2nc(Cl)ccc21] | 3.33 | 51.5 |
| P19 | 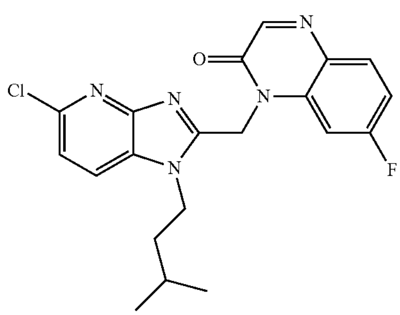 [SMILES: CC(C)CCn1c(Cn2c(=O)cnc3ccc(F)cc32)nc2nc(Cl)ccc21] | 0.042 | >100 |
| P20 | 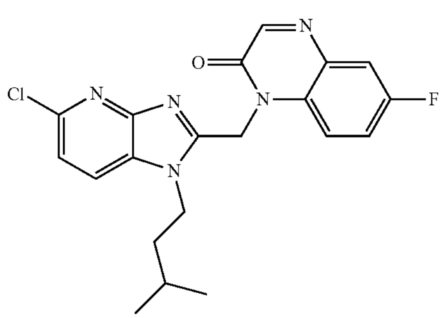 [SMILES: CC(C)CCn1c(Cn2c(=O)cnc3cc(F)ccc32)nc2nc(Cl)ccc21] | 0.032 | >100 |

-continued
| | Structure | WT activity EC$_{50}$ (μM) | Tox CC$_{50}$ (μM) |
|---|---|---|---|
| P21 | 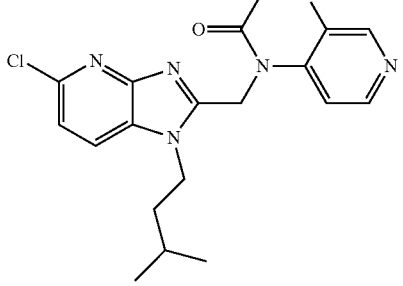 | >10.08 | >100 |
| P22 | 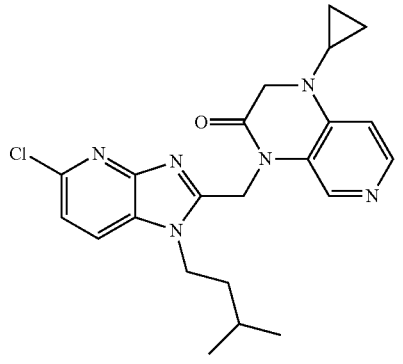 [SMILES: CC(C)CCn1c(CN2C(=O)CN(C3CC3)c3ccncc32)nc2nc(Cl)ccc21] | 0.12 | 60.66 |
| P23 | 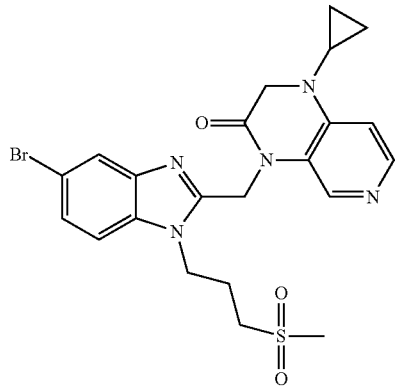 [SMILES: CS(=O)(=O)CCCn1c(CN2C(=O)CN(C3CC3)c3ccncc32)nc2cc(Br)ccc21] | 0.0015 | 71.33 |
| P24 | 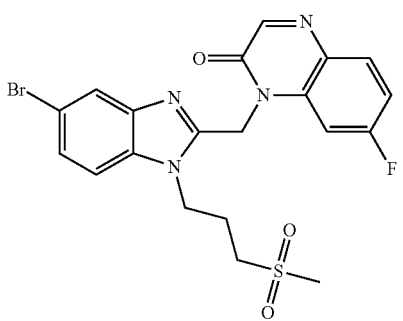 [SMILES: CS(=O)(=O)CCCn1c(Cn2c(=O)cnc3ccc(F)cc32)nc2cc(Br)ccc21] | 0.004 | 78.49 |

-continued
| | Structure | WT activity EC$_{50}$ (μM) | Tox CC$_{50}$ (μM) |
|---|---|---|---|
| P25 | 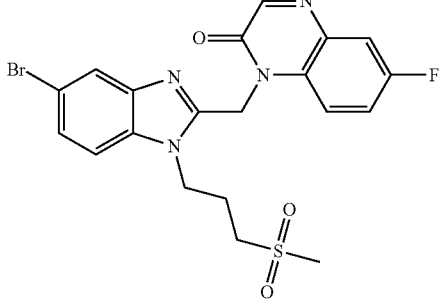 | 0.0065 | 63.97 |
| P26 | 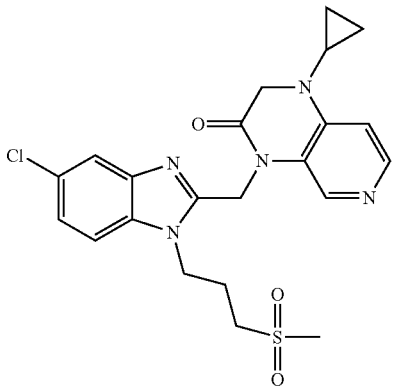 [SMILES: CS(=O)(=O)CCCn1c(CN2C(=O)CN(C3CC3)c3ccncc32)nc2cc(Cl)ccc21] | 0.015 | >100 |
| P27 | 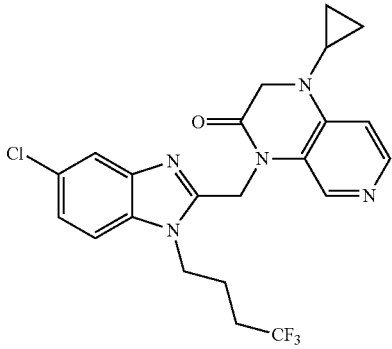 [SMILES: O=C1CN(C2CC2)c2ccncc2N1Cc1nc2cc(Cl)ccc2n1CCCC(F)(F)F] | 0.029 | >100 |
| P28 | 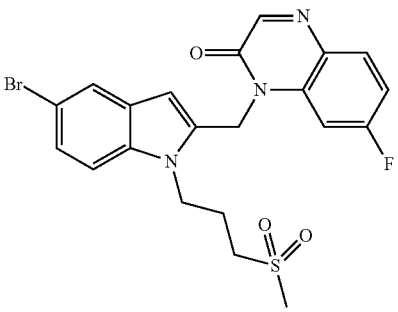 [SMILES: CS(=O)(=O)CCCn1c(Cn2c(=O)cnc3ccc(F)cc32)cc2cc(Br)ccc21] | 0.018 | NA |

| Structure | WT activity EC$_{50}$ (µM) | Tox CC$_{50}$ (µM) |
|---|---|---|
| P29 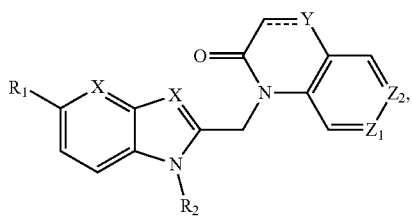 | 0.055 | 9.73 |

The invention claimed is:

1. A compound satisfying formula I

Formula I or a stereochemically isomeric or tautomeric form thereof wherein:
X is N;
Y is N or N—R$_4$;
Z$_1$ is N or C—R$_6$;
Z$_2$ is N or C—R$_3$;
R$_1$ is selected from the group consisting of H, halogen, C$_1$-C$_6$alkyl and C$_3$-C$_7$cycloalkyl;
R$_2$ is —(CR$_7$R$_8$)$_n$—R$_9$;
R$_3$ is selected from the group consisting of H, C$_1$-C$_6$alkyl, C$_3$-C$_7$cycloalkyl, CF$_3$ and halogen;
R$_4$ is selected from the group consisting of H, C$_1$-C$_6$alkyl and C$_3$-C$_7$cycloalkyl;
R$_6$ is selected from the group consisting of H, halogen, aryl and heteroaryl, wherein each of aryl or heteroaryl is optionally substituted with one or more R$_{10}$;
R$_7$ and R$_8$ are each independently selected from the group consisting of H, C$_1$-C$_6$alkyl and C$_3$-C$_7$cycloalkyl;
n is an integer selected from the range of 1 to 6;
R$_9$ is selected from the group consisting of H, halogen, SO$_2$R$_7$, C$_1$-C$_6$alkyl, CONR$_7$R$_8$, COOR$_7$, OH, CN, F, CFH$_2$, CF$_2$H and CF$_3$;
R$_{10}$ is selected from the group consisting of H, OH, CN, halogen, CFH$_2$, CF$_2$H, CF$_3$, CONR$_7$R$_8$, COOR$_7$ and C$_1$-C$_6$ alkyl, wherein each of R$_{10}$ is optionally substituted with one or more substituents selected from the group comprising NR$_7$R$_8$, CF$_3$, CH$_3$, OCH$_3$, OCF$_3$, morpholinyl and halogen;
or an addition salt or solvate thereof.

2. A compound according to claim 1, wherein R$_1$ is halogen.

3. A compound according to claim 1, wherein R$_2$ is —(CR$_7$R$_8$)$_n$—R$_9$, R$_7$ and R$_8$ are each independently hydrogen or CH$_3$, n is an integer of 3 or 4, R$_9$ is selected from the group consisting of halogen, CF$_3$ and SO$_2$R$_7$, and R$_7$ is CH$_3$.

4. A compound according to claim 1, wherein R$_6$ is selected from the group consisting of H, halogen, phenyl, pyridinyl, thiophenyl, pyrimidinyl, pyrazolyl, pyrrolyl, thiazolyl, each R$_6$ is optionally substituted with one or more R$_{10}$.

5. A compound according to claim 1, wherein R$_{10}$ is selected from the group consisting of halogen and C$_1$-C$_3$ alkyl, wherein each R$_{10}$ is optionally substituted with one or more substituents selected from the group consisting of NR$_7$R$_8$, CF$_3$, morpholinyl and halogen.

6. A compound according to claim 1, wherein R$_6$ is selected from the group consisting of phenyl, pyridinyl, thiophenyl, pyrimidinyl, pyrazolyl, pyrrolyl, and thiazolyl, each R$_6$ is optionally substituted with halogen.

7. A compound according to claim 1, wherein R$_2$ is C$_1$-C$_6$ alkyl optionally substituted with one or more of F or SO$_2$-Me.

8. A compound according to claim 1, wherein R$_4$ is cyclopropyl or H.

9. A compound of claim 1, wherein the compound is selected from the group consisting of:

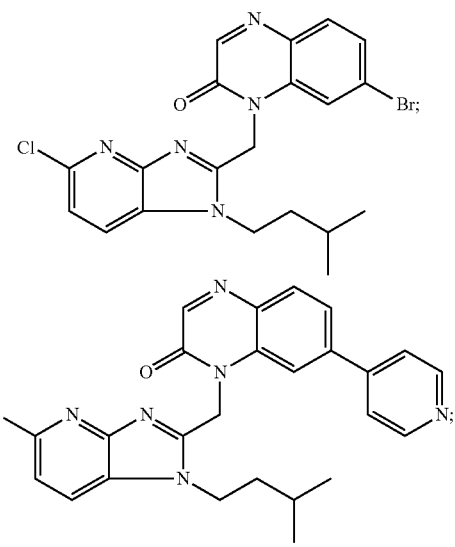

-continued

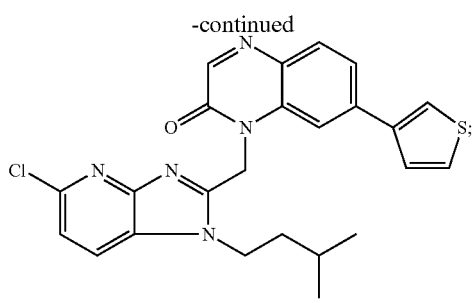

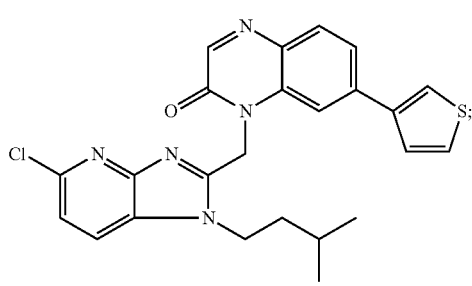

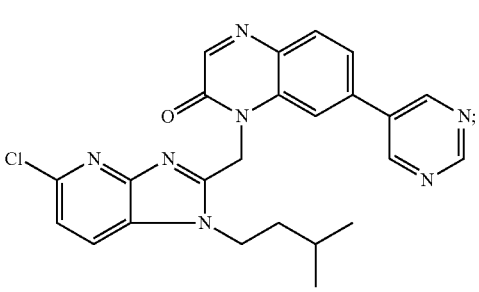

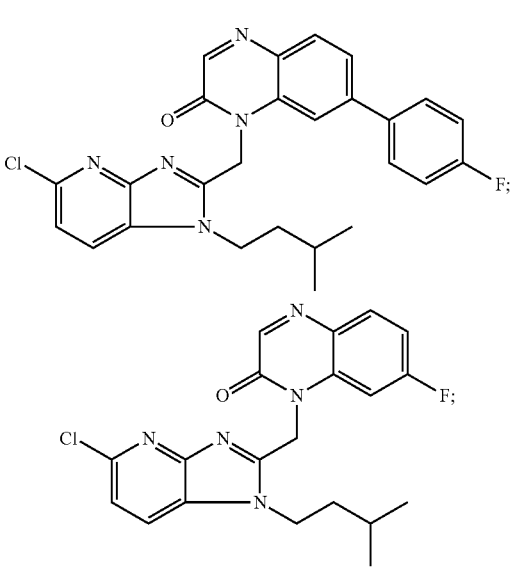

-continued

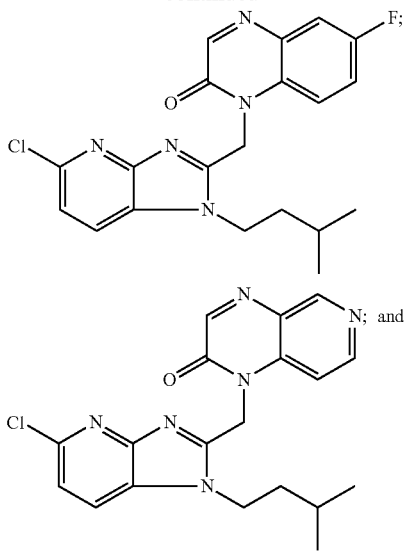

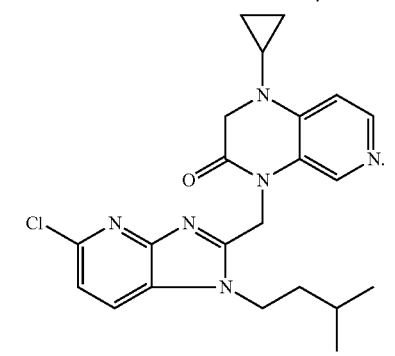

10. A pharmaceutical composition comprising a pharmaceutically acceptable carrier, and a compound of claim 1.

11. A process for preparing a pharmaceutical composition of claim 10, said process comprising mixing a pharmaceutically acceptable carrier with a therapeutically effective amount of a compound of claim 1.

12. A method of treating an RSV infection in a subject in need thereof, said method comprising administering to the subject a therapeutically effective amount of a compound of claim 1.

13. A method of inhibiting RSV replication in a subject in need thereof, said method comprising administering to the subject a therapeutically effective amount of a compound of claim 1.

14. The method of claim 12, wherein the subject is human.

15. The method of claim 13, wherein the subject is human.

16. A method of treating an RSV infection in a subject in need thereof, said method comprising administering to the subject the pharmaceutical composition of claim 10.

* * * * *